(12) United States Patent
van Bommel et al.

(10) Patent No.: US 7,534,915 B2
(45) Date of Patent: May 19, 2009

(54) NON-SYMMETRICAL GELLING AGENT

(75) Inventors: Kjeld Jacobus Cornelis van Bommel, Groningen (NL); Johannes Henricus van Esch, Groningen (NL)

(73) Assignee: Applied Nanosystems B.V., Groningen (NL)

( * ) Notice: Subject to any disclaimer, the term of this patent is extended or adjusted under 35 U.S.C. 154(b) by 279 days.

(21) Appl. No.: 11/432,735

(22) Filed: May 11, 2006

(65) Prior Publication Data
US 2006/0276676 A1 Dec. 7, 2006

Related U.S. Application Data

(63) Continuation of application No. PCT/NL2004/000723, filed on Oct. 14, 2004.

(30) Foreign Application Priority Data

Nov. 12, 2003 (EP) .................................. 03078599

(51) Int. Cl.
*C07C 229/46* (2006.01)
*A61K 48/00* (2006.01)
*A61K 9/127* (2006.01)

(52) U.S. Cl. ........................ 562/507; 560/126; 564/153; 514/616; 514/44; 424/450; 73/23.35

(58) Field of Classification Search ................. 562/507; 560/126; 564/153; 514/616, 44; 73/23.35; 424/450

See application file for complete search history.

(56) References Cited

U.S. PATENT DOCUMENTS

2005/0272677 A1* 12/2005 Friesen et al. ................. 514/44

FOREIGN PATENT DOCUMENTS

| JP | 2000072736 A | 3/2000 |
|----|---|---|
| WO | WO 00/35998 A2 | 6/2000 |
| WO | WO 00/35998 B1 | 6/2000 |
| WO | WO 03/084508 | 10/2003 |
| WO | WO 2005/047231 A1 | 5/2005 |

OTHER PUBLICATIONS

PCT Interntional Search Report, PCT/NL2004/000723, dated Nov. 29, 2004.
Appeldoorn et al., Rational Optimization of a Short Human P-selectin-binding Peptide Leads to Nanomolar Affinity Antagonists, The Journal of Biological Chemistry, Mar. 21, 2003, pp. 10201-10207, vol. 278, No. 12, USA.

* cited by examiner

*Primary Examiner*—Shailendra Kumar
(74) *Attorney, Agent, or Firm*—TraskBritt

(57) ABSTRACT

The present invention relates to a novel trisubstituted cyclic thickener or gelator. The present invention further relates to a method for thickening or gelating a solution comprising the use of such a gelator or thickener. A gelator or thickener according to the invention may, for instance, be used for pharmaceutical or cosmetic purposes. It may further be used as a support material in chromatographic materials or catalytically active materials.

26 Claims, 4 Drawing Sheets

NON-SYMMETRICAL GELLING AGENT

CROSS-REFERENCE TO RELATED APPLICATIONS

This application is a continuation of PCT International Patent Application No. PCT/NL2004/000723, filed on Oct. 14, 2004, designating the United States of America, and published, in English, as PCT International Publication No. WO 2005/047231 A1 on May 26, 2005, which application claims priority to European Patent Application No. 03078599.2, filed on Nov. 12, 2003, the contents of each of which are hereby incorporated herein by this reference.

TECHNICAL FIELD

The invention relates to a novel class of gelling agents/thickeners, to a process of preparing the agents/thickeners, to the use of gelling agents/thickeners to prepare gels/thickened solutions, and to the gels/thickened solutions thus obtained.

BACKGROUND

Thermally reversible gelling or thickening of organic solvents or water by low molecular weight thickener or gelators is of particular interest for hardening of spilled fluids and cooking oils, thickening of paints, cosmetic materials and several other technical applications. The self-assembly of these gelator/thickener molecules occurs by means of non-covalent interactions such as hydrophobic interactions, π-π interactions, electronic interactions, hydrogen bonding or combinations thereof. Although several gelator/thickener molecules have been identified during the last decade, there is still interest in stable gelator/thickeners that can be synthesized easily from cheap, renewable sources and gelate or thicken a wide variety of solvents.

WO 03/084508 describes trisubstituted cyclohexane compounds that may act as a gelator. These compounds, suitable as a gelator, are symmetrical in the sense that each of the substituents ($X_n$—$Am_n$—$Y_n$) comprises an amino acid or oligopeptide moiety (Am). Although the substituents may be different, it is preferred that they are the same.

WO 03/084508 also describes the compound

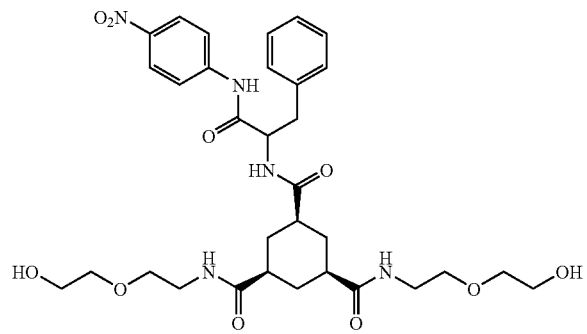

as a prodrug. The use of this compound as a gelator or thickening agent is not suggested. Rather, in order to make a stable gel, the prodrug is mixed with a gelator.

SUMMARY OF THE INVENTION

Provided is a novel class of gelling agents or thickeners. In certain embodiments, the invention provides gelling agents/thickeners that are based on readily available and economically attractive starting materials. In certain embodiments, the invention provides gelling agents/thickeners that are capable of gelling or thickening a wide variety of solvents, making the gelling agents or thickeners suitable in order to be employed in various applications.

It has been found that embodiments of the invention can be attained by preparing gelling agents or thickeners from amino acids, oligopeptides or derivatives thereof. A gelling agent or thickener according to the invention comprises a core (a ring comprising carbon atoms), which is functionalized in a specific way with three substituents of which at least one is an amino acid-derived group that is connected to the core by means of an amide, urea, thioamide, carbamate or thiocarbamate linkage.

Accordingly, the present invention relates to a non-symmetrical, trisubstituted cyclic organic compound, in particular a gelator or a thickener, of which the ring is substituted by one or two X—Am—$Y_n$ groups and wherein the remaining one or two substituents are —X-Z groups, wherein each of X is independently chosen from the moieties —N(H)—, —C(O)—, —NH—C(O)—, —O(CO)—, —OC(S)—, —C(S)— and —NHC(S)—;

each of Am is independently a moiety based on an amino acid or a derivative thereof, or a number of amino acids or derivatives thereof;

each of Y is independently chosen from the group of —OR, —N(OH)R, —$NR_2$, —C(O)R, —C(O)—$NR_2$, —C(O)—OR, —C(S)R, —C(S)—$NR_2$, —C(S)—OR and R, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms;

each Z is independently selected from the group consisting of —OH, —COOH, —C(O)NHR, —NHC(O)R and —NHR, wherein each R is independently chosen, and defined as above; and n=1 or 2.

The three substituents are preferably distributed essentially evenly around the ring structure, i.e., in a six-membered ring, the ring is preferably a 1,3,5 substituted ring.

A thickener or gelator of the invention is non-symmetrical in that at least two of the substituents of the trisubstituted gelator/thickener are different from each other; in particular, the —X-Z group should be different from the —X—Am—$Y_n$ groups, in case the thickener or gelator contains two identical —X—Am—$Y_n$ groups and the —X—Am—$Y_n$ should be different from the —X-Z groups in case the thickener or gelator contains two identical —X-Z groups. Preferably, the thickener or gelator according to the invention is non-symmetrical in the sense that at least one —X-Z group is present that does not represent any moiety that is represented by —X—Am—$Y_n$. More in particular, at least one of the substituents is preferably free of an Am group, as defined herein.

It has been found that a non-symmetrical compound according to the invention (in particular lacking C3-symmetry) is very suitable for making highly homogeneous, clear gels or thickened fluids, in particular, solutions. More in particular, it has been found that a gel according to the invention may comprise gel fibers with a relatively low thickness (for instance, of about 2 to 10 nm, e.g., about 5 nm).

It has been found that a thickener/gelator allows the preparation of a gel wherein gel structures (such as gel fibers) formed by the gelator/thickener are highly uniform in appearance (e.g., thickness).

Further, it has been found possible to prepare a highly transparent thickened fluid (solution) or gel with a thickener or gelator according to the invention.

Further, the invention provides a gelator/thickener that shows thixotropic behavior when present in a gel or thickened fluid (such as a thickened solution).

A gel/thickened fluid (solution) according to the invention is thus very appealing for applications, wherein a clear appearance is desired, such as in a cosmetic or pharmaceutical product for a topical application, e.g., an application to the eye, or a deodorant. Also such a feature is desired for use in a coating on a surface. A clear gel or thickened solution or other thickened fluid is defined herein, in particular, as a gel, solution, or fluid, respectively, that is substantially free of particles visible to the naked eye, which is transparent to at least some visible light.

An interesting aspect of the present invention is that the inventors have realized that a non-symmetric gelator or thickener may be provided with substituents with different hydrophilicity. Thus, gels are provided with a distinct structure, compared to the gelators such as those described in WO 03/084508, the contents of which are incorporated herein by this reference.

Due to the non-symmetric nature of the gelator/thickener according to the invention, the gelator/thickener may have a hydrophobic side (formed by one or two of the relatively hydrophobic substituents) and a hydrophilic side (formed by the remaining, relatively hydrophilic, substituent(s)).

Thus, the invention, in particular, relates to a trisubstituted thickener of gelator, wherein the X-Z group or groups are more hydrophilic than the X—Am—Y group or groups or wherein the X-Z group or groups are more hydrophobic than the X—Am—Y group or groups.

In particular, it is preferred that one or two of the groups are hydrophilic and the remaining group or groups are hydrophobic.

Examples of hydrophilic X-Z groups are COOH, C(O)NH $(CH_2)_2$OH C(O)NH$(CH_2)_2$O$(CH_2)_2$OH.

Examples of hydrophobic X—Am—Y groups are AmPheAmβNA, AmPheAmDecyl, AmPheAm-2Heptyl, AmMetAmβNA and AmTyrAmβNA. Very suitable as a hydrophobic group, is a —X—Am—$Y_n$ group, wherein the Am comprises a hydrophobic amino acid residue, in particular, an amino acid residue selected from Phe, Tyr, Met, Leu, Ala, Nle (norleucine). Other hydrophobic natural amino acid residues are the residues from Val, Trp and Ile. Furthermore, a hydrophilic Am (e.g., Ser) provided with a hydrophobic Y group may serve as a hydrophobic group, e.g., SerβNA8.

Without being bound by theory, it is contemplated that, when used as a gelator/thickener, a gel/thickened solution or other thickened fluid with fibers of the gelator/thickener may be formed that have a structure that is different from that of the symmetric gelators, as known from WO 03/084508. These particular non-symmetrical compounds according to the invention may be assembled in a stacked pie-like (wedged) structure with a hydrophobic interior and hydrophilic exterior (see, FIG. 7, right side, a non-symmetrical gelator according to the invention; left side, a symmetrical gelator).

Thus, with a non-symmetrical gelator/thickener according to the invention, it is now in principle possible to include separate molecules (e.g., bioactive molecules such as drugs) in the interior of the gelator stacks, allowing the solubilization and/or stabilization of hydrophobic molecules in hydrophilic solvents (e.g., water). As a symmetrical gelator/thickener does not inherently possess such a hydrophobic interior, they are not suitable for such a purpose. Accordingly, such a gelator/thickener according to the invention is particularly suitable for incorporating a hydrophobic substance, especially a substance having a solubility in water of less than about 10 mg/ml at 20° C.

Further, as a result of the fiber structure, which may be achieved with a gelator/thickener according to the invention, it is contemplated that the individual fibers have a lower tendency to aggregate into thicker bundles and hence the "fiber/bundle" thickness is generally thinner and also more homogeneous for a gelator/thickener according to the invention, leading to clearer gels.

It is also possible to use a compound as defined in claim 1 as an intermediate compound to prepare a further compound according to claim 1.

A thickener or gelator according to the invention can be represented by one of the following formulas, wherein A represents the ring (core) of the thickener or gelator and each X, Y, Z, respectively, Am can represent the same or different X, Y, Z, respectively, Am.

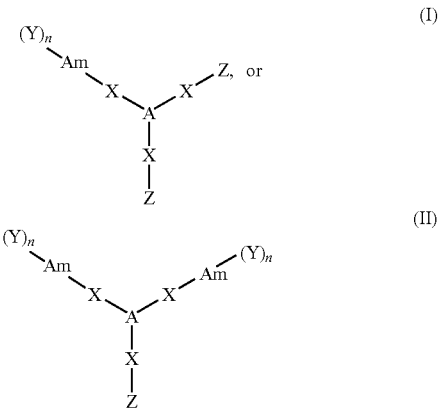

It has been found that a compound according to the invention is suitable as a gelling agent or thickener, in particular for an organic solvent, water or a mixture thereof. A thickener is defined herein as a compound that increases the viscosity of a solvent when dissolved therein. A gelator is an agent that can cause the gelling of a solvent under suitable circumstances. The term "gel" is generally understood in the art. In particular, a gel is usually defined as such when, upon inversion of a container in which it has been prepared, no immediate flow is observed. The gel may be formed from the gelator mixed with a solvent or another fluid, such as an emulsion, suspension or dispersion.

A compound according to the invention may be used as a chromatographic support for chiral recognition (separation of enantiomers, see, e.g., G. Gubitz et al., *Biopharm. Drug Dipos.* 22 (2001) 291-336).

Ranganathan et al. have disclosed in *Biopolymers*, 54 (2000) 289-295, crystal information of peptide dendrimers based on a benzene core to which branched structures of oligopeptides are connected. All disclosed compounds are based on glutamine as the only amino acid in the oligopeptides. It is mentioned that third generation dendrimers do not crystallize, but form gels. However, lower generation dendrimers crystallize.

PCT International Patent Application WO 03/084508 discloses gelators for carbon dioxide, which may be based on amino acids. Nothing is mentioned about gelation of other media. The disclosed compounds are highly fluorinated, which makes them less suitable for gelation or thickening of polar media, particularly aqueous media.

JP 2000 072736 discloses benzene tricarboxamides and their use as solidifying agent for waste oils, diesel fuel, lubricant oils and the like. The substituents to the benzene groups contain an —NHR group attached to an amino acid residue, in which R is an alkyl group from 8 to 22 carbon atoms. These groups are relatively apolar and bulky, making the disclosed benzene tricarboxamides less suitable for gelation or thickening of polar media, particularly aqueous media.

The cyclic organic thickener or gelator according to the invention may be a trisubstituted cycloalkyl, heterocycloalkyl, aromatic or heteroaromatic compound. Very good results have been achieved with a thickener or gelator, wherein the trisubstituted ring is formed by only carbon atoms.

The invention includes a gelator/thickener in any stereochemical orientation of the substituents. Very good results have been achieved with a gelator/thickener, wherein all substituents are in the equatorial position (i.e., in the case of a gelator/thickener with a cyclohexyl core, the compound has a "cis, cis"-configuration).

In the context of the invention, a cycloalkyl group is defined as a saturated or unsaturated cyclic alkyl group having from 4 to 18 carbon atoms. Preferred are cycloalkyl groups comprising 5- or 6-membered rings, in particular, cyclopentyl, cyclopentadienyl or cyclohexyl groups. It is to be noted that also annulated multiple ring systems are encompassed by the term cycloalkyl group. Examples are decahydranaphtalene, dodecahydraphenalene, and hexadecahydropyrene.

A heterocycloalkyl group is defined as a saturated or unsaturated cyclic alkyl group having one or more heteroatoms (i.e., atoms other than carbon atoms) in the ring. The heterocycloalkyl group preferably comprises one or more fused or coupled 4- to 16-, more preferably, 5- or 6-membered rings. Preferred heteroatoms that can be present in the ring are oxygen, sulphur and nitrogen. If present at all, it is preferred that one, two or three heteroatoms are present in the ring. These may be the same or different. It is to be noted that also annulated multiple ring systems are encompassed by the term heterocycloalkyl group. Examples are tetrahydropyran, tetrahydrothiopyran, dioxane, trans-hexahydro-isochroman, and trans-hydro-isothiochroman.

An aromatic group is defined as a cyclic group having an aromatic character comprising from 6 to 18 carbon atoms, wherein the ring system(s) only contains carbon atoms. It is to be noted that also fused or coupled multiple ring systems are encompassed by the term aromatic group. Examples are phenyl, naphthyl, anthracyl, and pyrene. Preferably, the trisubstituted aromatic ring is a trisubstituted benzene ring.

A heteroaromatic group is an aromatic group wherein one or more carbon atoms in a ring have been replaced by a heteroatom. Preferred heteroatoms that can be present in the ring are oxygen, sulfur and nitrogen. It is preferred that one, two or three heteroatoms are present in the ring. These may be the same or different. It is to be noted that fused or coupled multiple ring systems are also encompassed by the term heteroaromatic group. Examples are furan, pyridine, pyrazine, quinoline, and thiophene.

It is preferred that A represents a cyclohexyl or phenyl group. Preferably, the cyclohexyl or phenyl group is 1,3,5-substituted. In a more preferred embodiment, A represents a 1,3,5-susbstituted cyclohexyl group.

Each X may be the same or different. Accordingly, the Am and the Z groups can each independently be connected to A by attachment to a C═O, C═S, or a NH group. The choice for each X in the X—Am—$Y_n$ group will depend on whether the respective Am groups are to be attached at their $NH_2$-terminus or their COOH-terminus. If an amino acid or oligopeptide is connected through its $NH_2$-terminus, the particular X will be —C(O)—, —C(S)—, —OC(O)—, —OC(S)—, —NH—C(O)—, or —NHC(S)—. Likewise, if an amino acid or oligopeptide is connected through its COOH-terminus the particular X will be an NH group.

Each Am group is based on an amino acid or a derivative thereof. In principle, any group comprising at least one —NH or —$NH_2$ group and at least one —COOH group is considered an amino acid. It will be understood that each Am does not represent a complete amino acid. The amino acids are connected either through their $NH_2$-terminus to a corresponding X group and through their COOH-terminus to a corresponding Y group, or vice versa. The connection may, e.g., be an amide, urea, thioamide or a carbamate bond. Accordingly, one or two H-atoms of the $NH_2$-terminus, and the —OH of the COOH-terminus are not part of the overall structure.

It is also possible that any of the Am groups is based on more than one amino acid or a derivative thereof, and accordingly comprises a peptide, such as a di-, tri-, or higher oligopeptide. Preferably, each oligopeptide is based on up to 12, more preferably 2 to 5 amino acids, forming a linear peptide chain in which the amino acids are connected head-to-tail to one another. The amino acids may be chosen from all natural and unnatural (synthetic, e.g., β-amino acids or α-alkylated amino acids) amino acids. Preferably, the amino acids are α, β, or γ-amino acids, of which both the D and the L isomers are eligible. Particularly preferred are α-amino acids. Suitable examples of amino acids are leucine, isoleucine, norleucine, lysine, valine, proline, methionine, glycine, histidine, alanine, phenylalanine, tryptophan, serine, threonine, cysteine, tyrosine, asparagine, glutamine, aspartic acid, glutamic acid, and arginine.

Very good results have been achieved with a thickener or gelator wherein the Am group is based on phenylalanine or methionine. Another preferred Am group is based on cysteine. The presence of an —SH group in cysteine that can form a disulphide bridge may suitably be used to form a cross-linked gel. In the context of the invention, a derivative of an amino acid is defined as to include esters or amides (e.g., of aspartic acid, lysine or glutamic acid) and (thio)ethers (e.g., of serine, tyrosine or cysteine).

Each amino acid may be substituted with a substituent, wherein each substituent may be a substituted or unsubstituted, branched, cyclic or straight alkyl or alkenyl group that possibly contains an aromatic, ester or ether moiety or one or more other heteroatoms chosen from the group of N, S, O, P and B. Preferably, each substituent does not contain more than 12 carbon atoms. Preferably, each of the Am groups contains none or one substituent.

The end groups Y each may independently be chosen from the groups dependent on the nature of the corresponding X. For instance, if X is —C(O)—, —C(S)—, —OC(O)—, —OC(S)—, —NH—C(O)—, or —NH—C(S)—, Y may be —OR, —N(OH)R, and —$NR_2$. If X is, for instance, —NH—, Y may be —C(O)R, —C(O)—$NR_2$, —C(O)—OR, —C(S)R, —C(S)—$NR_2$, —C(S)—OR and R. Each of the R-groups mentioned in this regard, may be independently chosen from the group of H and substituted or unsubstituted, branched, cyclic or straight alkyl, alkenyl or alkynyl groups that possibly contain an aromatic, ester or ether moiety or one or more other heteroatoms and may have from 1 to 40 carbon atoms, and preferably has 12 carbon atoms or less. Very good results have inter alia been achieved with an R-group free of heteroatoms, such as with -naphthyl (—$C_{10}H_7$) or with —$CH_2$-phenyl (—$C_7H_7$).

If the R-group contains one or more heteroatoms, the heteroatoms are preferably chosen from O, N, S, P and B.

If n=2 or more, two (or more) Y groups on the same X—Am—$Y_n$ may be interconnected by an R-group (other than H).

In an embodiment, each Y is independently selected from —OH, —O-alk (wherein alk is a linear or branched alkyl group), linear or branched —O—$(CH_2)_i$—OH, —$NH_2$, linear or branched —$NH(CH_2)_iO(CH_2)_j$OH, linear or branched —$NH(CH_2)_iO(CH_2)_j$$CH_3$, linear or branched —$O(CH_2)_iO(CH_2)_j$$CH_3$, linear or branched —$O(CH_2)_iO(CH_2)_j$OH, —NHOH, —NH—$(CH_{2i+1})$ (wherein $(CH_{2i+1})$ is linear or branched), linear or branched —$NHC(CH_3)(CH_2)_i(CH_3)$, —$NH(CH_2)_i$OH, a naphthyl group, an —NH-naphthyl group, —NH—$(CH_2)_i$Ph (wherein $(CH_2)_i$ is linear or branched), —NH-Ph-O-alk (wherein alk is a linear or branched alkyl group, preferably a methyl) and —NH-quinoline. In groups i and j, each are preferably independently selected in the range of 1 to 9, more preferably in the range of 1 to 8, even more preferably, each independently are 1 or 2.

In an embodiment, each Y is independently selected from —$OCH_3$, —$OCH_2CH_3$, —O—$(CH_2)_2$—OH, —$NH_2$, —NH$(CH_2)_2O(CH_2)_2$OH, —$NH(CH_2)_2OCH_2CH_3$—$O(CH_2)_2$$CH_2CH_3$, —$O(CH_2)_2O(CH_2)$OH, —NHOH, —NH—$CH_3$, $NHC_{10}H_{21}$, —$NH(CH_2)_2$OH, a naphthyl group, an —NH-naphthyl group, —NH—$(CH_2)$Ph, —$NH(CH_2)_2$Ph, NH-Ph-OMe, $NHCH_2$Pyr, —$OCH_2$Ph and NH-quinoline.

In a preferred embodiment, each Y is selected from —OH, —$OCH_3$, —$OCH_2CH_3$, —$NHCH_3$, branched and linear —$NH(CH_2)_{x+1}$, wherein x is an integer from 1 to 9, branched and linear $NHC(CH_3)(CH_2)_{y+1}CH_3$, wherein y is an integer from 0 to 7, —$NH(CH_2)_9CH_3$, —$NH(CH_2)_{10}CH_3$, —NHC$(CH_3)(CH_2)_5(CH_3)$, —NH-Naphthyl, —$NHCH_2$Ph, —NH$(CH_2)_2$Ph, —NHPhOMe, —NH-Quinoline and $NHPhNO_2$.

In case the thickener or gelator comprises two —X—Am—$(Y)_n$ groups, both —X—Am—$(Y)_n$ groups are preferably the same.

In an embodiment, a gelator/thickener according to the invention, in particular, a gelator according to the invention contains a reactive group that can contribute to the gelling or thickening by forming cross-links. By choosing an appropriate reactive group, a gelling agent or thickener according to the invention may be used to form a gel or thickened fluid, in particular, a thickened solution, which can be subjected to further reaction. Any of the Am, Z and/or Y may contain such a reactive group. Examples of reactive groups are —C=C— groups (e.g., in the R moiety of Y or Z) and —SH groups (e.g., in the Am moiety).

For instance, a gelling agent or thickener with a reactive group, e.g., a terminal alkenyl group (C=C), can, after formation of a viscous fluid (in particular a viscous solution) or gel in an aromatic solvent be interconnected by a metathesis reaction following standard procedures as found in, e.g., J. Am. Chem. Soc. (1995) 117, 12364. The metathesis reaction transforms the viscous solution or gel into a stiff gel, which can, for instance, be used in columns for chromatographic purposes (see also Sinner et al., Angew. Chem. Int. Ed. 39 (2000) 1433-1436, and Sinner et al., Macromolecules 33 (2000) 5777-5786).

Besides, it is possible to achieve the gelling or thickening by letting the reactive group react with a chemical, e.g., one may react a gelator/thickener according to the invention comprising a thiol group with a bis-maleimide or the like, to achieve cross-linking. Suitable reaction conditions are as those known in the art for other cross-linking reactions.

The Z group may be a group as defined for Y. Preferably, each —X—Z is chosen independently from the group consisting of —COOH; —C(O)NHR, wherein R is more preferably H or an alkyl, even more preferably H or —$CH_3$; —NHC(O)R; —NHR; C(O)—NH—$(CH_2)_i$—OH, wherein i preferably is 1 to 8, for instance 2; C(O)—NH—$(CH_2)_i$—O—$(CH_2)_j$—OH, wherein i, j are preferably 1 to 8, for instance 2; and C(O)NH$(CH_2)_i$-pyr, wherein i preferably is 1, 2 or 3. Any of these X-Z groups have been found particularly suitable in case the substituted ring of the thickener or gelator is a substituted cyclohexane or substituted benzene.

In particular, in case of a 1,3,5-substituted cyclohexane or a 1,3,5-substituted benzene compound, very good results with respect to gelling or thickening have been achieved with a thickener or gelator, wherein —X-Z is chosen from the group of —COOH, —C(O)—$NH_2$, —C(O)—$NHCH_3$, —C(O)—NH—$(CH_2)_2$—OH, —C(O)—NH—$(CH_2)_2$—O—$(CH_2)_2$—OH, C(O)OCH$_2$Ph and C(O)NHCH$_2$-pyr.

Preferably, all substituents —X—Am—Yn and —X-Z of the gelator/thickener are such that the gelator/thickener is a non-zwitterionic compound. Thus, when dissolved in a pH-neutral solution, such as water (pH 7 at 25° C.), the gelator/thickener preferably is either essentially non-ionic, essentially cationic or essentially anionic.

It has been found that a zwitterionic trisubstituted compound according to formula I or II, such as a compound comprising a carboxylic acid group and an amine group tends to be less effective as a gelator. Without being bound by theory, it is contemplated that the zwitterionic character of the compound hinders gelation to some extent, in particular, when used in a protic solvent such as water or an aqueous solution.

Typical methods of preparing a gelling agent or thickener according to the invention will now be described with reference to two preferred groups of compounds. It will be understood by the skilled person that many variations in the synthesis are possible without leaving the scope of the invention. The skilled person will know how to prepare other gelators/thickeners according to the invention based upon the information provided in the present description and claims and common general knowledge.

BRIEF DESCRIPTION OF THE FIGURES

FIG. 3 shows initial rate as a function of the concentration of substrate (S)

DETAILED DESCRIPTION OF THE INVENTION

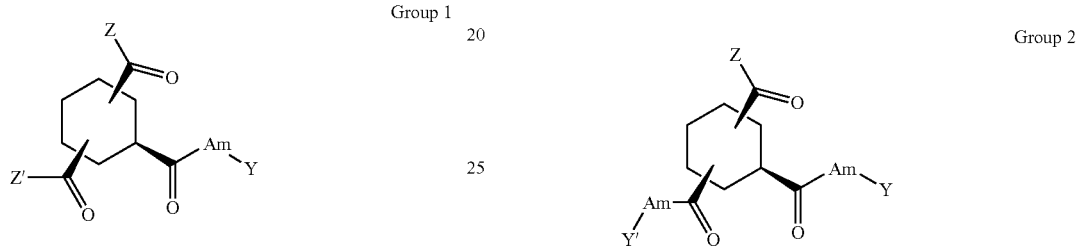

Group 1

Group 2

Figure 1:
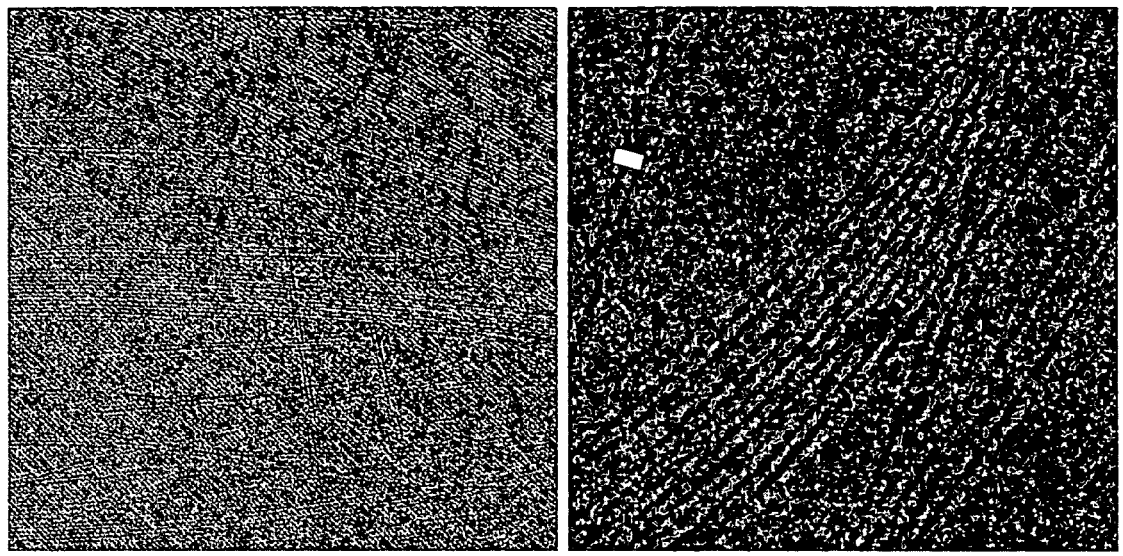
FIG. 1 shows an example of a cryo TEM image of a hydrogel sample of the gelators described herein The left-side image is low magnification, while the right-side image is high magnification (white bar at the upper left-hand quarter in the right-side image corresponds to 4.5 nm).

A thickener or gelling agent according to this formula (with Z=Z'=OH) can be prepared by reaction of a cyclohexanetricarboxylic acid, optionally, after activation of the carboxylic acid group, with a free amino group of an amino acid derivative, such as an amino acid alkyl ester or amide, or an amino acid aryl ester or amide (according to standard organic procedures for amide and ester formation (of amino acids) as described in inter alia, M. Kunishama, C. Kawachi, J. Morita, K. Tereao, F. Iwasaki, S. Tani, *Tetrahedron* (1999) 13159-13170; M. B. Smith, J. March, *March's Advanced Organic Chemistry*, 2001, 5$^{th}$ edition, Wiley Interscience; E. Muller, O. Bayer, Houben-Weyl, *Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans.* 2, (1996) 2707-2713; H. Tamiaki, A. Kiyomori, K. Maruyama, *Bull. Chem. Soc. Jpn*, 66, (1993) 1768-1772; S. Bhattacharya, S. N. G. Acharya, *Chem. Mater.* (1999) 3121-3132). By using a large excess of the cyclohexanetricarboxylic acid in this reaction, the formation of di- and tri-functionalized cyclohexanes can be limited. Isolation of the monoadduct can be accomplished by standard organic chemistry procedures, including crystallization/precipitation, column chromatography, extraction, etc.

Alternatively, a cyclohexanetricarboxylic derivative may be synthesized of which two of the carboxylic acid moieties are capped with protecting groups (e.g., converted to benzyl esters, but also other protecting groups may be used: see T. W. Greene, P. G. M. Wuts, Protective groups in organic synthesis, 1999, 3$^{rd}$ edition, Wiley Interscience). Reaction of the remaining carboxylic acid with a free amino group of an amino acid derivative (as described above), followed by removal of the protecting groups on the carboxylic acids (in the case of benzyl esters, H$_2$+Pd/C can be used; for the removal of other protective groups, see T. W. Greene, P. G. M. Wuts, Protective groups in organic synthesis, 1999, 3$^{rd}$ edition, Wiley Interscience) then gives the monoadduct.

The thusly obtained monoadducts (with Z=Z'=OH) can be used for the formation of numerous derivatives by conversion of C(O)Z and/or C(O)Z' (with Z=Z'=OH) to give compounds in which Z and/or Z' are chosen from the group of —OR, NHR, NHC(O)R, wherein each R is independently chosen and defined as above (other than R=H, which represents the monoadduct starting material). Such conversions can be carried out following standard organic procedures known to the person skilled in the art. Subsequent reaction steps may be carried out to further alter the structure of the compounds. An example of such a step is the hydrolysis (under alkaline conditions) of methyl esters of amino acids to give the corresponding free acids.

A thickener or gelling agent according to this formula (with Z=OH) can be prepared by reaction of a cyclohexanetricarboxylic acid, optionally after activation of the carboxylic acid groups, with a free amino group of an amino acid derivative, such as an amino acid alkyl ester or amide, or an amino acid aryl ester or amide (according to standard organic procedures for amide and ester formation (of amino acids) as described in a.o. M. Kunishama, C. Kawachi, J. Morita, K. Tereao, F. Iwasaki, S. Tani, *Tetrahedron* (1999) 13159-13170; M. B. Smith, J. March, *March's Advanced Organic Chemistry*, 2001, 5$^{th}$ edition, Wiley Interscience; E. Muller, O. Bayer, Houben-Weyl, *Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans.* 2, (1996) 2707-2713; H. Tamiaki, A. Kiyomori, K. Maruyama, *Bull. Chem. Soc. Jpn*, 66, (1993) 1768-1772; S. Bhattacharya, S. N. G. Acharya, *Chem. Mater.* (1999) 3121-3132). A mixture of mono, bis- and triadduct will be formed, from which the bisadduct can be isolated by standard organic chemistry procedures, including crystallization/precipitation, column chromatography, extraction, etc.

Alternatively, a thickener or gelling agent according to this formula (with Z=OH) can be prepared by using a cyclohexanetricarboxylic acid derivative of which one of the carboxylic acid moieties is capped with a protecting group (e.g., converted to a benzyl, but also other protecting groups may be used: see T. W. Greene, P. G. M. Wuts, Protective groups in organic synthesis, 1999, 3$^{rd}$ edition, Wiley Interscience). Reaction of the remaining carboxylic acids, each with a free amino group of an amino acid derivative (as described above), followed by removal of the protecting group on the carboxylic acid (in the case of benzyl esters, H$_2$+Pd/C can be used; for the removal of other protective groups see T. W. Greene, P. G.

M. Wuts, *Protective groups in organic synthesis*, 1999, 3rd edition, Wiley Interscience), then gives the bisadduct.

The thusly obtained bisadducts (with Z=OH) can be used for the formation of numerous derivatives by conversion of C(O)Z (with Z=OH) to give compounds in which Z is chosen from the group of —OR, NHR, NHC(O)R, wherein R is chosen, and defined as above (other than R—H which represents the bisadduct starting material). Such conversions can be carried out following standard organic procedures known to the person skilled in the art. Subsequent reaction steps may be carried out to further alter the structure of the compounds. An example of such a step is the hydrolysis (under alkaline conditions) of methyl esters of amino acids to give the corresponding free acids.

Typically, trisubstituted compounds described herein have been found to be able to thicken or gel in one or more out of numerous solvents, including aromatic, non-aromatic hydrocarbons, alcohols, ethers, esters, aldehydes, ketones, alkanoic acids, epoxides, amines, halogenated hydrocarbons, silicon oils, vegetable oils, phosphoric acids, sulfoxides, amides, nitriles, water and mixtures thereof. The term "mixture" as used herein includes not only mono-phase fluidic systems (solutions) but also emulsions, dispersions, suspensions and other multi-phase fluidic systems. By using the appropriate compounds or mixtures thereof, the range of gelated or thickened solvents or other gelated/thickened fluids can be tuned and the solvents or other fluids can either be gelated or thickened.

In a preferred embodiment, water or an aqueous solvent is gelated. In accordance with this embodiment, the gelling agent preferably has a 1,3,5-substituted cyclohexyl core (A in formula (I) or (II) above). X in the X-Z is preferably —C(O)— and X in the X—Am—$Y_n$ is preferably —C(O)— and in case there are two X—Am—$Y_n$, each Am is preferably the same and chosen from the group of α, β and γ-amino acids, of which both the D and the L isomers are eligible. Very good results have been achieved with phenylalanine or methionine. Another preferred amino acid is cysteine; such a compound according to the invention contains a cross-linkable —SH group, which is advantageous for the gelling/thickening properties of a gelling agent/thickener according to the invention.

The present invention further relates to a method of gelating or thickening a solvent comprising mixing an appropriate amount of gelling agent or thickener according to the invention with the solvent.

A gelator/thickener according to the invention has been found particularly suitable for preparing a hydrogel, i.e., wherein the solvent is water or an aqueous solution, wherein water is the major component. It has been found possible to prepare very clear hydrogels in accordance with the invention.

A suitable concentration of the thickener or gelator depends upon the solvent and the thickener or gelator. In practice, good results have been achieved with an amount of the thickener or gelator between 0.01 and 50 wt. %, based on the weight of the composition. Preferably, the amount of thickener or gelator in the gel/thickened fluid/thickened solution is 0.1 to 50 wt. %, in particular 0.4 to 50 wt. %.

The mixing may be sufficient to cause gelling. Optionally, the thickening or gelling is triggered by an addition of a gelling-inducing component and/or an environmental stimulus to obtain the thickened or gelated solvent.

Preferably, the mixing of the components is performed by heating (in some cases, it may be helpful to homogenize the components, e.g., vortex) them together at temperatures of 20 to 200° C., preferably 50 to 150° C. Cooling these hot mixtures to a preferred temperature in the range of −20 to 100° C., preferably to 4 to 100° C., more preferably to 15 to 30° C., affords the gel or thickened solvent or other thickened fluid. The obtained gels have been found to comprise thin, intertwining fibers. In an alternative embodiment, the gelling agent is first dissolved in a polar or apolar solvent and then added or sprayed into a composition, solvent or other fluid to be converted into a gel. Of course, it is also possible to add or spray a composition or solvent to be converted into a gel into a solution of the gelling agent in a polar or apolar solvent.

Another method to produce gels includes the use of light, pH and/or chemical stimuli as environmental stimuli. Photo-controlled gelation and pH controlled gelation are two mechanisms that can be used to induce the sol-to-gel transition, while in some cases, this process is reversible and thus can also be used for gel-to-sol transition. Chemical inducers for triggering gel-to-sol or sol-to-gel formation are, e.g., disulfide-reducing enzymes and thiol-oxidizing enzymes, which in nature also occur in the human body. Also, tris-(2-carboxyethyl)phosphine, mercaptoethanol, 1,4-dithiothreitol, glutathione and dimethyl sulfoxide (DMSO) can be used for chemical triggering.

One further way to form a gel is by mixing solutions of two different gelling agents, which each independently at the reaction temperature and concentration remain in the sol phase, but when mixed transit to the gel phase.

Another form of an environmental stimulus is sonication. A gel may, for instance, suitably be made by a method wherein the gelling agent is mixed with the solvent under influence of sonication and the formation of a gel is triggered by stopping sonication.

A gel comprising a thickener or gelator according to the invention can be used as a chromatographic support for chiral recognition or for covalent binding of a catalyst.

In a further aspect, the invention relates to a gel or thickened solvent or other thickened fluid comprising a gelator/thickener according to the invention and particles of a substance of interest, in particular, particles having a diameter in the range of 1 nm to 100 μm, preferably in the range of 1 to 250 nm, more preferably in the range of from 1 to 100 nm. The particles preferably comprise a biologically active agent, preferably a pharmaceutically active agent. A gel comprising a thickener or gelator according to the invention can be used as delivery vehicle for a substance of interest, e.g., for a drug.

Such use may be analogous to the use of a gelator/thickener as a drug delivery vehicle, e.g., as disclosed in International Patent Application WO 03/084508. In accordance with this embodiment, the gels can be used as the vehicle in delivery vehicles for delivering a substance of interest, in particular a drug, to a predetermined site in vivo, the vehicle comprising the substance and a means for inducing availability of at least one compartment of the vehicle toward the exterior, thereby allowing access of the substance to the exterior of the vehicle at the predetermined site.

Preferably, the substance to be made available in an induced way at the predetermined site, is incorporated in the gel at the time of gel formation. However, this need not always be the case. Substances may also be allowed to enter a preformed gel under the appropriate conditions. For releasing the drug, use may be made of a transition of the gel into a sol.

Surprisingly, it has been found that formation of gels comprising a drug for controlled delivery can be used to produce very small particles of the drug, which have been found to be impossible to produce in conventional manners such as milling. This is particularly important for (oral) administration of drugs that are not soluble or poorly soluble in water or aqueous systems. To achieve the small particle size, the drug may be dissolved in an organic solvent, such as dimethyl sulfoxide (DMSO) or ethanol, together with a gelling agent or thickener according to the invention. Upon addition of water, gel formation occurs. Simultaneously, the water insoluble/poorly water-soluble drug precipitates in the form of very small particles (typically of less than 500 nm, or even about 70 nm or less). If desired, the DMSO or ethanol can be washed out of the system, leaving an aqueous gel containing the small drug particles. This may be used as such (in the form of a "wet" gel) or lyophilized and formulated into a pharmaceutical product. It is possible to wash out the gelling agent or thickener, leaving only the small drug particles for use in the formulation of a pharmaceutical product.

Besides for the formation of particles of drugs, the thickener/gelling agent may be used for forming different kinds of particles. In particular, it may be used for preparing a cosmetic ingredient, a pigment (e.g., for use in a coating/paint) or a fluorophore (such as pyrene).

In a preferred embodiment for a system wherein a gelator/thickener is present in a delivery system for a substance of interest, such as a biologically active agent (more in particular, a pharmaceutically active agent), the unintended leakage of the substance to be made available out of the gel is low or may even be negligible. This is preferably achieved by allowing for an interaction of the substance with the gel. The interaction can be achieved using a covalent bond of any type. In the case of a covalent bond, at least one of the substituents of the gelator/thickener comprises a cleavable moiety, which upon cleavage, results in release of the substance of interest. The substance of interest may be bound to the gelator/thickener via a non-covalent bond (such as electrostatic or hydrophobic interactions, H-bonds). Such an embodiment is referred to herein as a complex. Release of the substance from the gel can be achieved in a number of ways known to the person skilled in the art and depending on the type of gel, substance and environment. Covalent bonds can also comprise labile links, which can be broken under certain conditions such as pH, temperature, enzyme activity, light and the like. Using such labile linkers between the substance of interest and the gelling agent nearly totally prevents leakage and enables the immediate release of the substance of interest when the environmental conditions supersede the threshold for breaking the link. Preferably, the enzymatically labile linker is cleaved by an enzyme that is present in the neighborhood of the target cell. If a substance of interest is covalently linked via an enzymatically labile linker to either a gelling agent or a prodrug-gelling agent conjugate (which can be incorporated into the gel structure), enzymatic cleavage in the gel state should be strongly disfavored. The gel-to-sol transition, however, will make the prodrug available to the enzyme, resulting in cleavage and subsequent release of the drug. Very good results have been achieved with α-chymotrypsin as the enzyme, in particular, in combination with a linker comprising an amino acid moiety, such as an L-phenylalanine moiety, that is cleavable at its C=O terminus.

The invention will now be further illustrated by the following examples.

EXAMPLES

The used abbreviations represent the following:
DMSO=dimethyl sulfoxide
CDI=1,1-carbonyl diimidazole
DMT-MM=4-(4,6-dimethoxy-1,3,5-triazin-2-yl)-4-methylmorpholinium chloride
β-NA=β-naphthyl
MeOH=methanol
Phe=phenylalanine
Met=methionine
Bn=benzyl
TFA=trifluoroacetic acid
Ph=phenyl
EA=ethyl acetate
iPrOH=iso-propanol
6-AQ=6-aminoquinoline
EtOH=ethanol
PEG 400=polyethylene glycol (400)
MeCN=acetonitril
PG=propylene glycol
TBA=ter-butylalcohol
p-NA=para-nitroaniline Several compounds were synthesized (described below in Examples I and II). A number of these compounds were subjected to one or more of the following tests.

Gel Test

A weighed amount of solid was dissolved in 0.5 or 1 ml of the solvent in a closed 2.0 ml vial using a heating gun or a heating block and subsequently slowly cooled to room temperature by standing in the air. Gelation was determined by turning the vial upside down and gentle shaking. If no flow of the mass was observed, the mass was defined to be a gel. Alternatively, a weighed amount of solid was dissolved in 1 mL of solvent by the addition of acid or base. The subsequent addition of base or acid then gave gelation. Alternatively, a weighed amount of solid was dissolved in a small amount of solvent. The subsequent addition of a large amount of non-solvent then gave gelation. Alternatively, the solution of gelator/thickener was added to the non-solvent, resulting in gelation. Alternatively, a weighed amount of solid was mixed with 1 mL of solvent by sonication. After stopping the sonication, gelation occurred. Alternatively a weighed amount of solid was mixed with 1 mL of solvent by brief vortexing after which gelation occurred. Alternatively a weighed amount of solid was mixed with 1 mL of solvent after which gelation occurred.

Determination of Melting Temperature

Melting temperatures of the gels ($T_{gel}$) were determined by the dropping ball method (H. M. Tan, A. Moet, A. Hiltner, E. Baer, Macromolecules 1983, 16, 28).

Transmission Electron Microscopy Measurements

A gel was prepared following one of the procedures described above. A small amount of the gel was carefully deposited on a carbon-coated copper grid, using a spatula. The excess solution was blotted with a filter paper, leaving a thin sample film. The samples were examined using a JEOL 1200EX (80-100 kV) and pictures were taken of representative parts. The samples were all prepared in duplo.

Cryo-transmission Electron Microscopy Measurements

A gel was prepared following one of the procedures described above. A small amount of the gel was carefully deposited on a bare copper grid, using a spatula. The excess solution was blotted with a filter paper, leaving a thin sample film. The grid was subsequently plunged into liquid ethane for vitrification. The vitrified specimens were transferred to a Gatan model 626 cryostage and observed in a Philips CM 120 electron microscope operating at 120 kV. The images were recorded under low-dose conditions at about −170° C. The samples were all prepared in duplo.

Example I

Synthesis of Compounds Represented by the General Formula

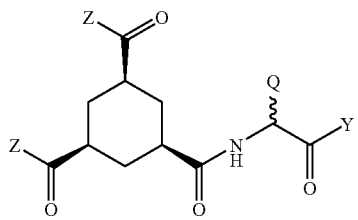

CHex(AmPhe-AmβNA)(COOH)₂ (1)

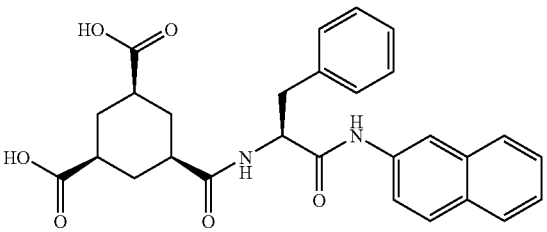

To a solution of cis,cis-1,3,5-cyclohexanetricarboxylic acid (11.18 g; 51.71 mmol) and HOBT (2.55 g, 18.87 mmol) in DMSO (200 mL) was added CDI (2.80 g, 17.27 mmol). After stirring for two hours at room temperature, Phe-βNA (5.00 g, 17.22 mmol) was added and stirring was continued overnight after which the solution was poured into H₂O (600 mL), resulting in the formation of a gelly precipitate. The precipitate was filtered off and washed repeatedly with H₂O (4×100 mL) and once with cold MeOH (50 mL). The remaining gelly solid was dissolved in hot acetone (ca. 400 mL) and filtered, after which the solvent was removed in vacuo. The remaining solid was further purified by dissolving it in a mixture of hot MeOH (400 mL) and 2N NaOH (aq) (200 mL). After filtration of the solution, it was poured onto a mixture of ice (ca. 150 mL) and concentrated HCl (aq) (50 mL). The resulting precipitate was filtered off, washed with H₂O (2×150 mL), dissolved in acetone. (ca. 200 mL) and filtered over a double paper filter. The filtrate was concentrated in vacuo to give pure 1 as a white solid. Yield: 5.20 g (10.64 mmol=61.8%).

Gel test: 3 mg/mL in H₂O: slightly crystalline gel.

CHex(AmPhe-AmβNA)(AmEtOEtOH)₂ (2)

A solution of compound 1 (1.50 g, 3.16 mmol), 2(-2-aminoethoxy)-1-ethanol (1.00 g, 9.49 mmol), and DMT-MM (1.92 g, 6.95 mmol) in MeOH (65 mL) and DMSO (20 mL) was stirred overnight at room temperature. The gelly precipitate that had formed, was filtered off, washed with H$_2$O (4×50 mL), and dissolved in hot MeOH/H$_2$O (20:1, 150 mL). The solution was filtered and subsequently evaporated to dryness by repeated azeotropic distillation with toluene to remove all the water. Compound 2 was isolated as a white solid. Yield: 1.20 g (1.85 mmol=58.6%).

Gel test: 1 mg/mL in H$_2$O: clear gel.
CHex(AmMet-AmβNA)(COOH)$_2$ (3)

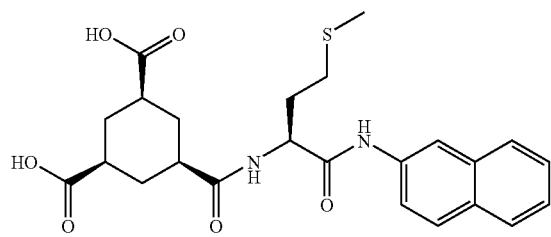

This compound was synthesized according to the procedure described for compound 1, using Met-βNA (3.00 g, 10.93 mmol). After the reaction, the DMSO (75 mL) was poured into H$_2$O (500 mL). The resulting precipitate was filtered off, washed with H$_2$O (3×200 mL), and dissolved in hot MeOH/H$_2$O (20:1, 200 mL), after which the solution was filtered and subsequently evaporated to dryness by repeated azeotropic distillation with toluene to remove all the water. Compound 3 was isolated as a white solid. Yield: 4.70 g (9.95 mmol=91.0%).

Gel test: 3 mg/mL in H$_2$O: slightly crystalline gel.
CHex(AmMet-AmβNA)(AmEtOEtOH)$_2$ (4)

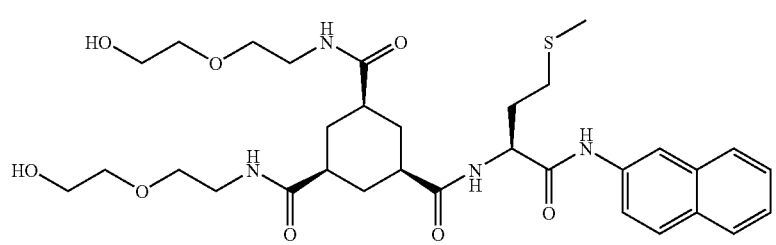

This compound was synthesized according to the procedure described for compound 2, using compound 3 (2.00 g, 4.23 mmol). The gelly precipitate that had formed after reaction, was filtered off, washed with H$_2$O (4×50 mL), washed with hot MeOH (3×100 mL), and finally dried in vacuo to give pure 4 as a white solid. Yield: 2.20 g (3.41 mmol=80.7%).

Gel test: 1 mg/mL in H$_2$O: clear gel; 3 mg/mL in MeOH: clear gel.
CHex(AmMet-AmβNA)(AmEtOH)$_2$ (5)

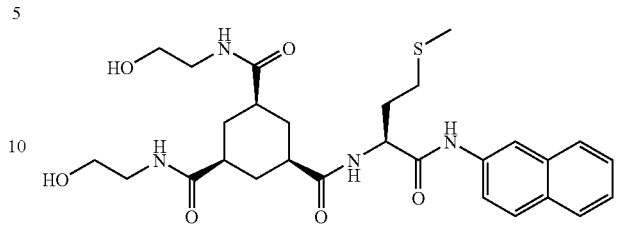

This compound was synthesized according to the procedure described for compound 4, using ethanolamine (0.39 g, 6.35 mmol). Yield: 0.78 g (1.40 mmol=65.8%).

Gel test: 2 mg/mL in H$_2$O: clear gel.
CHex(AmMet-AmβNA)(AmCH$_2$Pyr)$_2$ (6)

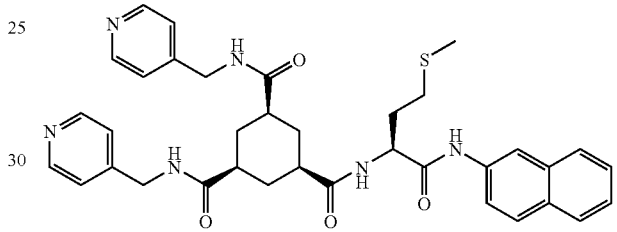

This compound was synthesized according to the procedure described for compound 4, using 4-picolylamine (0.34 g, 3.18 mmol). The gelly precipitate that had formed after reaction, was filtered off, washed with MeOH (2×20 mL), and dried in vacuo. The crude product was dissolved in a mixture of MeOH and 2N HCl (aq) (50 mL each) and the resulting solution filtered over a paper filter. The filtrate was brought to a pH of 12 by addition of 5N NaOH and the resultant precipitate was filtered off, washed with H$_2$O (2×50 mL) and dried in vacuo to give pure 6 as an orange-brown solid. Yield: 0.41 g (0.63 mmol=59.2%).

Gel test: 1 mg/mL in H$_2$O: slightly turbid gel.
CHex(AmPhe-AmBn)(COOH)$_2$ (7)

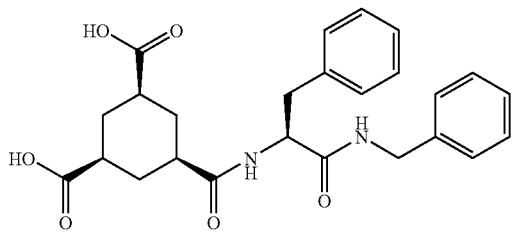

This compound was synthesized according to the procedure described for compound 1, using Phe-AmBn.TFA (4.00 g, 9.88 mmol) and Et₃N (2.0 g, 20.0 mmol). The gelly precipitate that had formed, was filtered off, washed with H₂O (3×100 mL), and extracted with MeOH (3×100 mL cold, 3×30 mL hot). Evaporation of the combined extracts gave pure 7 as a white solid. Yield: 2.00 g (4.42 mmol=44.8%).

Gel test: 3 mg/mL in H₂O: slightly turbid gel.

CHex(AmPhe-AmBn)(AmEtOEtOtH)₂ (8)

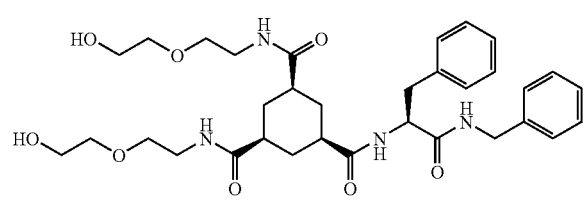

This compound was synthesized according to the procedure described for compound 2, using compound 7 (2.00 g, 4.42 mmol) and MeOH (120 mL) as the solvent. The gelly precipitate that formed was filtered, washed with MeOH (2×50 mL), dissolved in hot MeOH/H₂O (3:1, 800 mL), and filtered. The filtrate was evaporated to dryness to give pure 8 as a white solid. Yield: 1.80 g (2.87 mmol=65.0%).

Gel test: 1 mg/mL in H₂O: clear gel (thixotropic); EtOH: gel; PG: gel; t-BuOH: gel; mixtures H₂O/PG or H₂O/t-BuOH: gel; olive oil: weak gel; MeCN: gel; PEG 400: gel.

To a hydrogel of 8 (2 mg/ml) was added olive oil (200 μL). The mixture was vortexed for five seconds to give a gelated emulsion.

CHex(AmPhe-AmPh-OMe)(COOH)₂ (9)

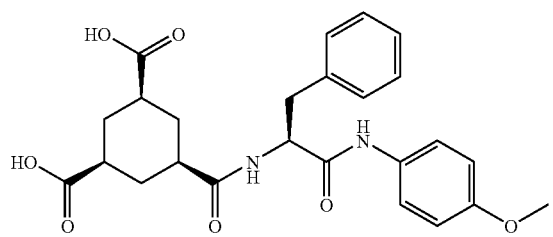

This compound was synthesized according to the procedure described for compound 3, using Phe-AmPh-OMe (1.95 g, 7.22 mmol). The final product was recrystallized/regellated from MeOH to give pure 9 as a white solid. Yield: 2.85 g (6.09 mmol 84.3%).

Gel test: 3 mg/mL in H₂O: clear gel.

CHex(AmPhe-AmPh-OMe)(AmEtOEtOH)₂ (10)

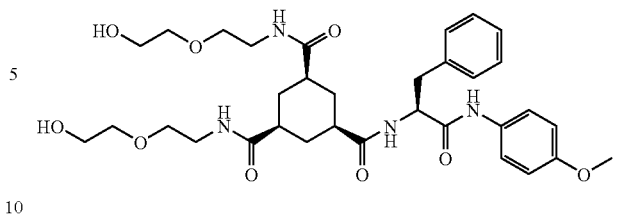

This compound was synthesized according to the procedure described for compound 2, using compound 9 (0.95 g, 2.03 mmol). The final product was recrystallized/regellated from MeOH to give pure 10 as a white solid. Yield: 0.76 g (118 mmol=58.3%).

Gel test: 3 mg/mL in H₂O: clear gel.

CHex(AmPhe-6AQ)(AmEtOEtOH)₂ (12)

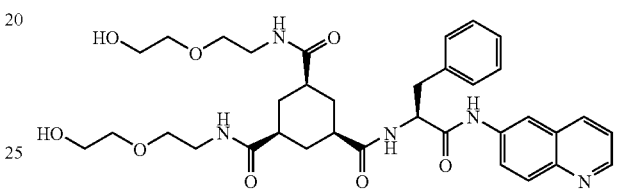

Step I: CHex(AmPhe-6AQ)(COOH)₂ (11)

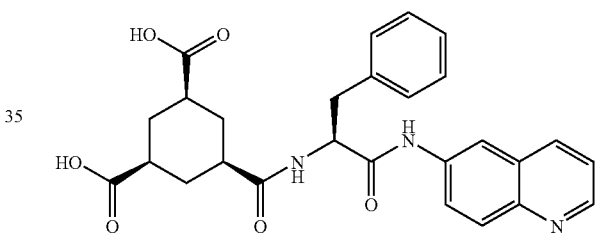

This compound was synthesized according to the procedure described for compound 1, using Phe-6AQ.2HBr (4.51 g, 10.0 mmol) and Et₃N (4.04 g, 40.0 mmol). The solid that was collected by filtration was dissolved in DMSO/H₂O/acetone and filtered, after which the acetone was slowly evaporated, resulting in the formation of a precipitate that was collected by filtration and subsequently dried to give pure 11 as a light orange solid. Yield: 2.95 g (6.03 mmol=60.3%).

Step II: CHex(AmPhe-6AQ)(AmEtOEtOH)₂ (12)

This compound was synthesized according to the procedure described for compound 2, using 11 (2.80 g, 5.73 mmol). After completion of the reaction H₂O (300 mL) was added and the resultant precipitate was filtered off, washed with H₂O (3×100 mL), and dried. The crude product was purified by column chromatography (SiO₂, CH₂Cl₂:MeOH=9:1-8:2) to give pure 12 as a light yellow solid. Yield: 1.60 g (2.41 mmol=42.1%).

Gel test: 0.3 mg/mL in H₂O or PBS: clear gel; 0.5 mg/mL in H₂O/DMSO (19:1): clear gel; 0.6 mg/mL in H₂O/EtOH (19:1): clear gel; 25 mg/ml in EtOH: turbid gel.

Cryo-TEM investigation, as well as small angle x-ray diffraction were carried out on one compound (12) and it proved that the gel consisted of fibers with a uniform thickness of about 4.5 nm (corresponding to the length of two molecules). Presumably, the lack of (C3-)symmetry prevents the aggregation of the fibers into large bundles from taking place, and leads to the highly uniform and very low fiber diameter, the latter in turn leading to clear gel.

A cryo-TEM picture of a gel of compound 12 (0.4 wt % hydrogel) is shown in FIG. 1. FIG. 1 shows a typical example of a cryo-TEM image of a hydrogel sample of the gelators described in the present description. The left-side image is a low magnification, the right-side image a high magnification (white bar at the upper left-hand quarter in the right-side image corresponds to 4.5 nm). FIG. 1 clearly shows the densely intertwined fibrous structure that is responsible for the immobilization of the solvent. The high uniformity of the fiber thicknesses can be clearly observed in the close-up image on the right.

CHex(AmAlaAmβNA)(COOH)$_2$ (13)

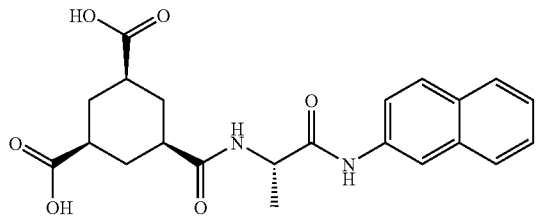

This compound was synthesized according to the procedure described for compound 1, using AlaβNA.

Gel test: water: gel.

CHex(AmPheAmPhNO$_2$)(AmEtOEtOH)$_2$ (14)

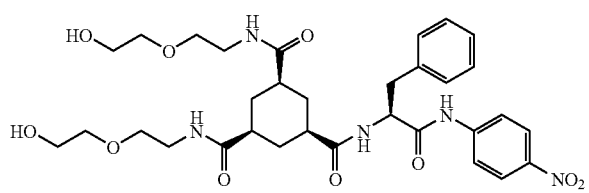

This compound was synthesized in two steps according to the procedures described for compounds 1 and 2.

In step I, the reaction mixture was poured into slightly acidic water and the resulting precipitate was filtered off, rinsed with water (3×200 mL), dissolved in acetone, dried with MgSo$_4$ and evaporated to dryness to give the pure dicarboxylic acid compound. Yield: 8.04 g (16.63 mmol=95.0%).

In step 11 the precipitate was filtered, rinsed with MeOH (3×40 mL), and dissolved in CH$_2$Cl$_2$/MeOH (1/1, ca 700 mL). The mixture was filtered and the filtrate was evaporated to dryness to give pure 14 as a white solid. Yield: 3.3 g (5.02 mmol=69.3%).

Gel test: upon heating of the compound in water, hydrolysis of the PheAmPhNO$_2$ amide takes place as observed by the yellow color (p-NA). Upon cooling down, a yellow, weak gel is formed.

CHex(AmPheAmCHex)(AmEtOEtOH)$_2$ (18)

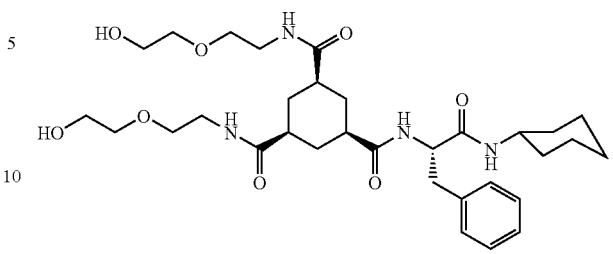

Step I: CHex(OBn)$_2$(COOH) (15)

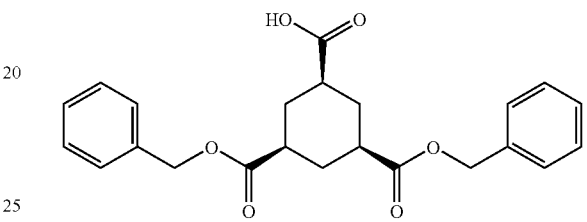

To a solution of cis,cis-1,3,5-cyclohexanetricarboxylic acid (50.0 g; 0.24 mol) in DMSO (750 mL) was added CDI (46 g, 0.29 mol). After the CO$_2$ evolution had stopped (ca. two hours), benzylalcohol (35 mL, 0.34 mol) was added and the solution was stirred overnight at 60° C., after which the main part of the solvent was removed in vacuo. Subsequently, the crude product was partitioned between EA (1000 mL) and 1N HCl (aq) (1000 mL) and the organic layer was extracted with H$_2$O (2×500 mL), brine (500 mL), dried with MgSO$_4$, and evaporated to dryness to give an oil that was purified by column chromatography (SiO$_2$, CH$_2$Cl$_2$:MeOH=100:0-80:20) to give 15 as a white solid. Yield: 25.6 g (64.64 mmol=26.9%).

Step II: CHex(OBn)$_2$(AmPheAmCHex) (16)

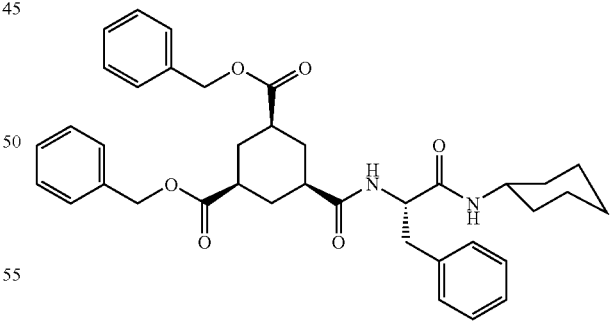

To a stirred, cooled (0° C.) solution of 15 (5.15 g, 13.0 mmol) and HOBT (1.82 g, 13.5 mmol) in EA (200 mL) was added CDI (2.18 g, 13.5 mmol). The solution was allowed to come to room temperature and stirring was continued for two hours, after which a solution of Et$_3$N (2.83 g, 28.0 mmol) and PheAmCHex.TFA (14.44 mmol) in EA (50 mL) were added dropwise. The mixture was stirred for 1½ days, after which the precipitate was filtered off, washed with EA (3×100 mL), and dried to give pure 16 as a white solid. Yield: 3.95 (6.32

Gel test: olive oil: gel; EtOH: gel; MeCN: gel; PEG 400: gel

Step III: CHex(COOH)₂(AmPheAmCHex) (17)

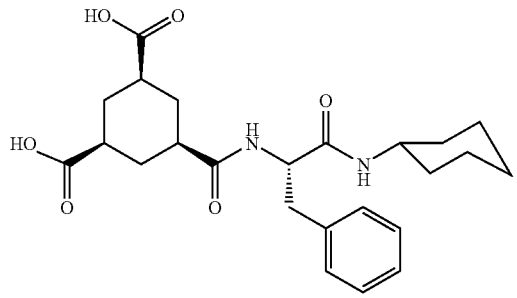

This compound was synthesized according to the procedure described for compound 30, using 16 (3.50 g, 5.60 mmol). Yield: 1.47 g (3.31 mmol=59.1%).

Step IV: CHex(AmEtOEtOH)₂(AmPheAmCHex) (18)

This compound was synthesized according to the procedure described for compound 2, using compound 17. The formed precipitate was filtered off, washed with MeOH (3×50 mL), and dried to give pure 18 as a white solid. Yield: 1.42 g (2.17 mmol=71.4%).

Gel test: 2 mg/mL in H₂O: clear gel; 20 mg/mL in DMSO: turbid gel

CHex(AmPheAmDecyl)(COOH)₂ (19)

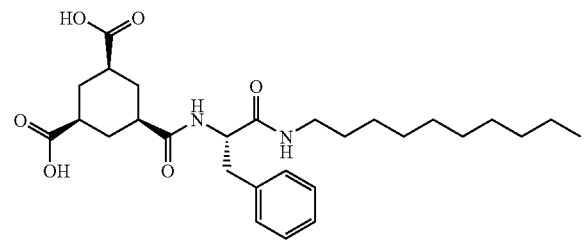

This compound was synthesized in two steps according to the procedures described for compounds 16 and 17, using PheAmDecyl. Yield step I: 0.65 g (0.95 mmol=17.1%); yield step II: 0.45 g (0.90 mmol=94.4%).

Gel test: H₂O: clear gel; toluene: gel

CHex(AmPheAmDecyl)(AmEtOEtOH)₂ (20)

This compound was synthesized according to the procedure described for compound 18, using compound 19.

Gel test: H₂O: gel; EtOH: gel; PEG: gel; toluene: gel

CHex(AmPheAm2-Heptyl)(COOH)₂ (21)

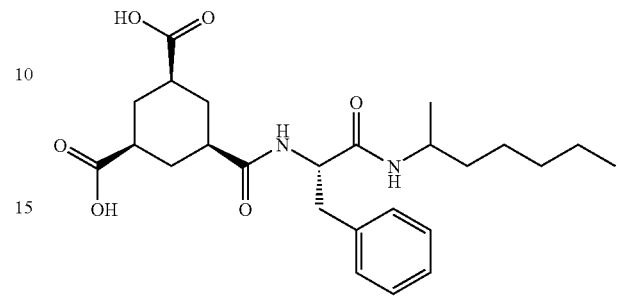

This compound was synthesized in two steps according to the procedures described for compounds 16 and 17, using PheAm2-Heptyl. Yield step I: 2.00 g (3.13 mmol=50.5%); yield step II: 1.25 g (2.72 mmol=96.7%).

Gel test: H₂O: gel; toluene: gel

CHex(AmPheAmPheOMe)(COOH)₂ (22)

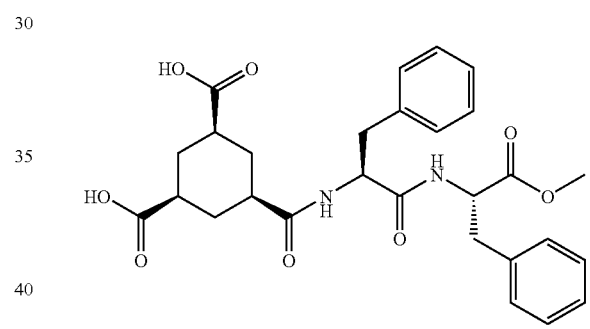

This compound was synthesized in two steps according to the procedures described for compounds 16 and 17, using PheAmPheOMe. Yield step I: 1.60 g (2.27 mmol=45.0%); yield step II: 0.60 g (1.15 mmol=53.8%).

Gel test: toluene: gel

CHex(AmPheAmPheOH)(COOH)₂ (23)

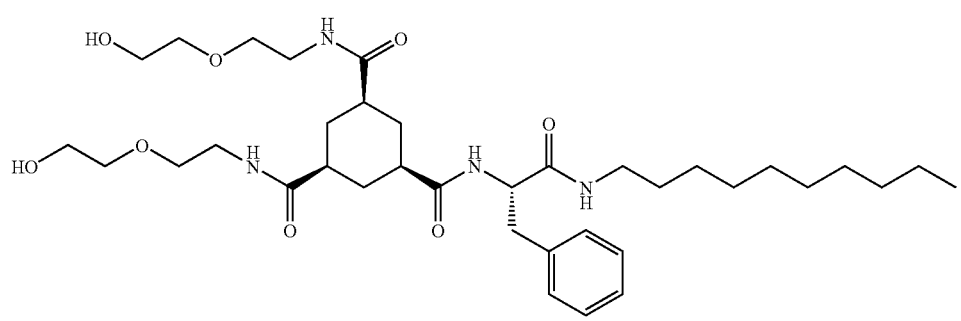

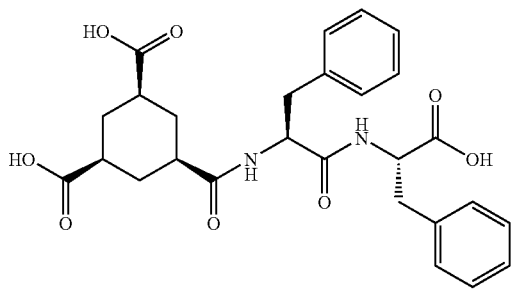

An aqueous gel of this compound was made by heating a suspension of compound 22 in 1N NaOH (aq) until clear. Addition of 2N HCl (aq) to the cooled (RT) solution resulted in the formation of a gel compound 23.

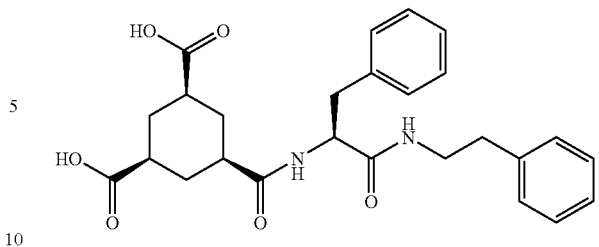

This compound was synthesized in two steps according to the procedures described for compound 16 (connection of the amino acid) and step III of the synthesis of compound 24 (i.e., deprotection of the carboxylic acids through basic hydrolysis), using PheAmEtPh. Yield step I: 2.20 g (3.41 mmol=46.8%); yield step II: 1.28 g (3.02 mmol=97.5%).

Gel test: H₂O: gel; toluene: gel.

CHex(AmPheAmEtPh)(AmEtOEtOH)₂ (26)

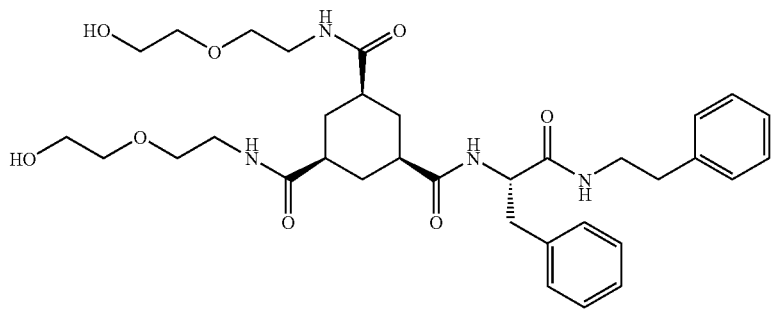

CHex(AmTyrAmβNA)(AmEtOEtOH)₂ (24)

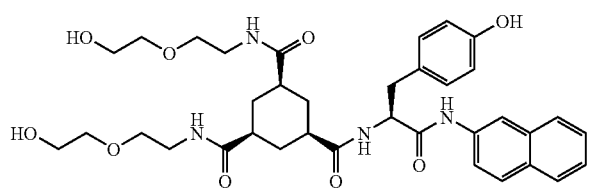

This compound was synthesized in four steps according to the procedures described for compound 18 using TyrβNA.

Step III, cleavage of the benzyl moieties, however, was carried out through basic hydrolysis in DMSO/2N NaOH (aq) (30+10 mL) for 15 minutes (1 g scale). The mixture was then poured into ice/water (150 mL) and was acidified using concentrated acetic acid, resulting in the precipitation of a white solid that was filtered off, rinsed with water (4×50 mL) and acetone (50 mL), and dried to give the pure dicarboxylicacid compound. Yield: vvv (menno).

In step IV of the synthesis, the formed precipitate was reprecipitated from MeOH/acetone/H₂O (slow evaporation) and isolated through centrifugation and freeze-drying. Yield: 0.14 g (0.21 mmol=20.8%).

Gel test: 1 mg/mL in H₂O: clear gel; olive oil: gelly precipitate; EtOH: gel; MeCN: gel.

CHex(AmPheAmEtPh)(COOH)₂ (25)

This compound was synthesized according to the procedure described for compound 18, using compound 25. Yield: 0.9 g (1.40 mmol=61.1%).

Gel test: H₂O: gel (thixotropic); propylene glycol(PG): gel; t-BuOH: gel; mixtures H₂O/PG or H₂O/t-BuOH: gel.

CHex(AmPheAmGlyAmβNA)(COOH)₂ (27)

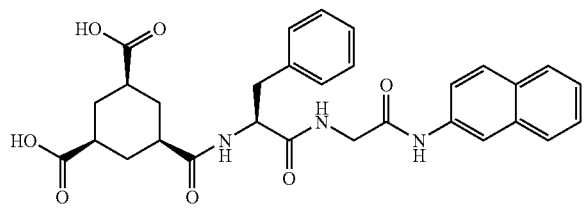

This compound was synthesized in two steps according to the procedures described for compound 16 (connection of the amino acid) and step III of the synthesis of compound 24 (i.e., deprotection of the carboxylic acids through basic hydrolysis), using PheAmGlyAmβNA. Yield step I: 1.30 g (1.79 mmol=63.3%); yield step II: 0.28 g (0.51 mmol=39.0%).

Gel test: H₂O: gel.

Example II

Synthesis of Compounds Represented by the General Formula

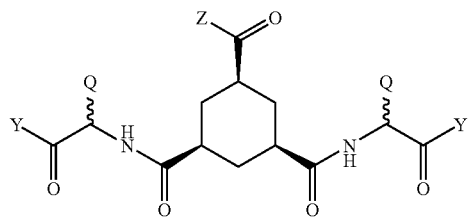

CHex(AmPhe-OMe)$_2$(COOH) (30)

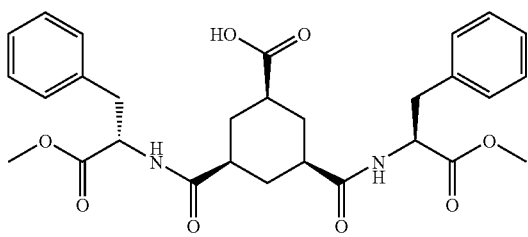

Step I: CHex(OBn)(COOH)$_2$ (28)

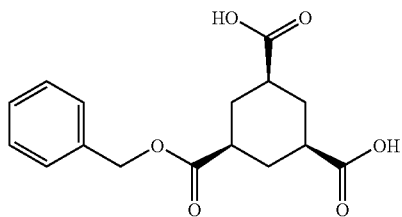

To a solution of cis,cis-1,3,5-cyclohexanetricarboxylic acid (25.00 g; 0.12 mol) in DMSO (250 mL) was added CDI (18.75 g, 0.12 mol). After the CO$_2$ evolution had stopped (ca. two hours), benzylalcohol (12.4 g, 0.12 mol) was added and the solution was stirred overnight at 60° C., after which the main part of the solvent was removed in vacuo. Subsequently, the crude product was partitioned between EA (500 mL) and 1N HCl (aq) (500 mL) and the aqueous layer was extracted with EA (2×250 mL). The combined organic layers were dried with MgSO$_4$ and evaporated to dryness to give an oil that was purified by column chromatography (SiO$_2$, CHCl$_3$: MeOH=99:1-98:2) to give 28 as a white solid. Yield: 15.1 g (49.30 mmol=41.1%).

Step II: CHex(AmPhe-OMe)$_2$(OBn) (29)

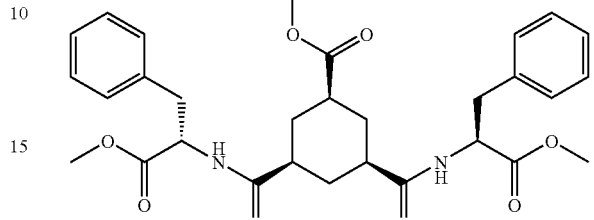

A solution of 28 (3.06 g, 10.00 mmol), Phe-OMe.HCl (4.73 g, 22.00 mmol), Et$_3$N (3.03 g, 30.00 mmol), and DMT-MM (6.08 g, 22.00 mmol) in MeOH (50 mL) was stirred overnight at room temperature. The gelly precipitate that had formed was filtered off and washed with MeOH (50 mL). The crude product was then dissolved in CH$_2$Cl$_2$ (200 mL), washed with 1N HCl (3×100 mL) and brine (100 mL), and dried with MgSO$_4$. Recrystallization from CH$_2$Cl$_2$/MeOH (ca. 75+100 mL) gave pure 29 as a white solid. Yield: 2.8 g (4.45 mmol=44.5%).

Gel test: Olive oil: gel; toluene: gel; EtOH: gel; MeOH: gel.

Step III: CHex(AmPhe-OMe)$_2$(COOH) (30)

To a solution of 29 (2.40 g, 3.81 mmol) in MeOH/iPrOH/CH$_2$Cl$_2$ (100+100+200 mL) was added 10% Pd/C (50 mg) and the mixture was stirred vigorously under a H$_2$ atmosphere for three days, after which the catalyst was removed by filtration over a double paper filter. The solution was then evaporated to dryness to give pure 30 as a white solid. Yield: 2.00 g (3.71 mmol=97.4%).

Gel test: 3 mg/mL in H$_2$O: clear gel; olive oil: gel; toluene: gel; EtOH/H$_2$O and PEG 400/H$_2$O mixtures: gel.

CHex(AmNleOMe)$_2$(COOH) (31)

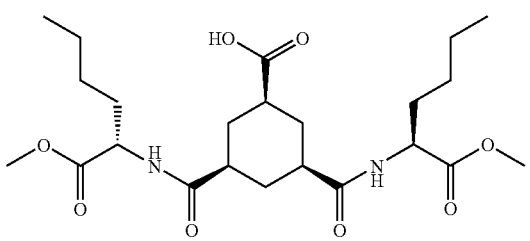

This compound was synthesized in three steps according to the procedures described for compound 30. In step II, Nle-OMe was used i.s.o. PheOMe.

Gel test: EtOH: gel; PEG400: gel.

29

CHex(AmNleOH)₂(COOH) (32)

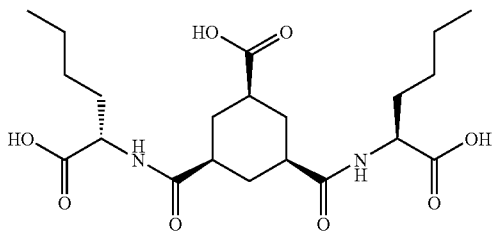

A mixture of 31 (0.20 g, 0.43 mmol) in MeOH (2 mL), 2N NaOH (aq) (20 mL), EtOH (10 mL), and H₂O (50 mL) was heated until nearly clear and then sonicated for 10 minutes. Subsequently, the solution was filtered and acidified with 1N HCl (90 mL). The formed precipitate was filtered off, washed with H₂O (3×50 mL) and dried in vacuo to give pure 32 as a white solid. Yield: 0.17 g (0.38 mmol=89.4%).

Gel test: H₂O: gel.

30

CHex(AmPheAmMe)₂(COOBn) (33)

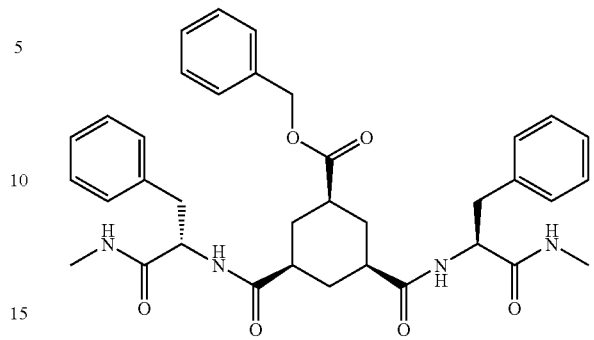

This compound was synthesized in according to the procedure described for compound 29, using PheAmMe. Yield final step: 1.47 g (2.35 mmol=42.8%).

Gel test: DMSO: turbid gel.

CHex(AmPheAmβNA)₂(COOH) (34)

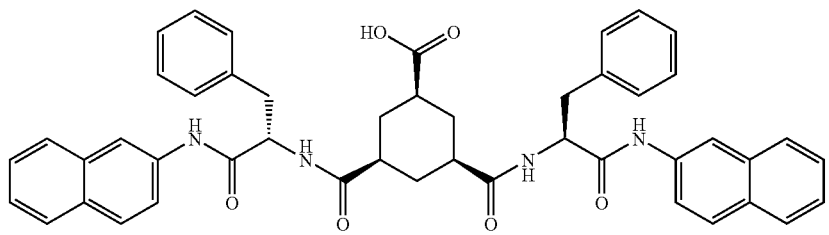

This compound was synthesized in two steps starting from compound 28. Step I was carried out according to the procedure described for compound 29, using PheβNA. In step I, the precipitate was filtered off, rinsed with MeOH (3×40 mL), and dried to give the benzyl-protected precursor in 96.2% yield. Step II was carried out according to step III of the synthesis of compound 24. Yield: 0.71 g (0.93 mmol=79.2%).

Gel test: H₂O: gel; TBA/H₂O mixtures: gel.

CHex(AmSerAmβNA)₂(COOBn) (35)

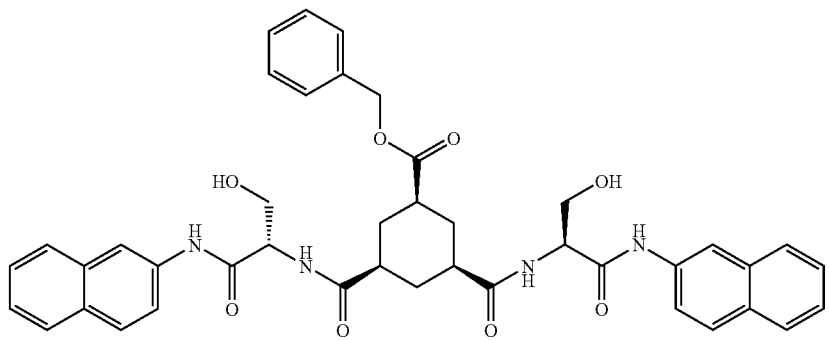

This compound was synthesized according to step I of the procedure described for compound 34, using SerβNA. Yield: 4.2 g (5.75 mmol=88.1%).

Gel test: EtOH: gel; MeCN: gel; DMSO/MeOH, DMSO/toluene, DMSO/EtOH, DMSO/MeCN, DMSO/CH$_2$Cl$_2$ mixtures: gel.

CHex(AmSerAmβNA)$_2$(COOH) (36)

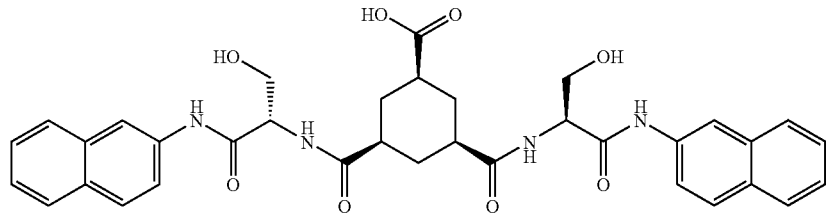

This compound was synthesized according to step II of the procedure described for compound 34, using compound 35. Yield: 1.35 g (2.11 mmol=68.5%).

Gel test: H$_2$O: gel; MeCN: weak gel; TBA/H$_2$O, DMSO/toluene, DMSO/EtOH, DMSO/MeCN, DMSO/H$_2$O, DMSO/CH$_2$Cl$_2$ mixtures: gel.

CHex(AmLeuAmβNA)$_2$(COOH) (37)

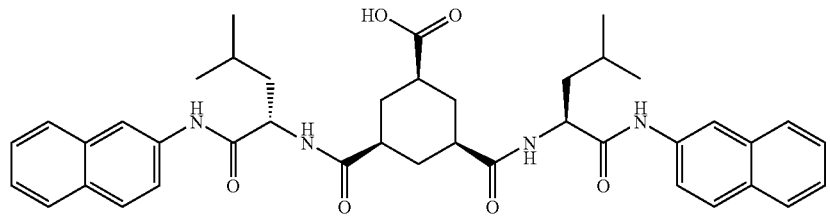

This compound was synthesized according to the procedures described for compounds 35 and 36, using LeuβNA. Yield step I: 1.40 g (1.79 mmol=87.3%). Yield step II: 0.68 g (0.98 mmol=80.6%).

Gel test: H$_2$O/TBA, H$_2$O/iPrOH, H$_2$O/MeOH, and H$_2$O/DMSO mixtures: gel.

CHex(AmGlnAmβNA)$_2$(COOH) (38)

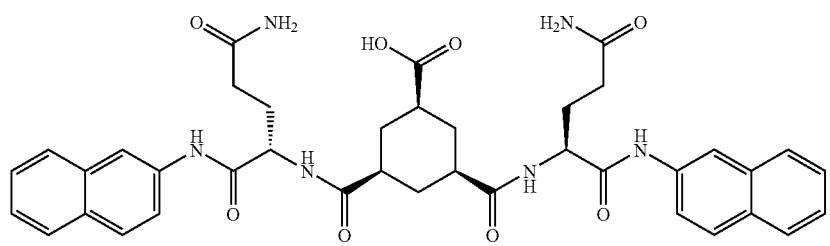

This compound was synthesized according to the procedures described for compounds 35 and 36, using GlnβNA. Yield step I: 1.10 g (1.35 mmol=91.5%). Yield step II: 0.71 g (0.98 mmol=80.0%).

Gel test: H$_2$O: gel.

Example III

Enzymatic Cleavage of a Gelator-drug Conjugate

In order to investigate the enzymatic cleavage of a gelator-drug conjugate, we selected the enzyme α-chymotrypsin, which is capable of cleaving amide bonds at the C=O terminus of L-phenylalanine-based substrates like compound 12 (CHex(AmPhe-6AQ)(AmEtOEtOH)$_2$), resulting here in the release of the fluorogenic "model drug" 6-aminoquinoline (6-AQ). This system allows easy monitoring of the cleavage kinetics owing to the fact that the excitation and emission maxima for the amide and amino form of this compound are adequately separated (amide form: $\lambda_{ex}$=315 nm, $\lambda_{em}$=370 nm, amine form: $\lambda_{ex}$=339 nm, $\lambda_{em}$=550 nm). Compound 12 indeed proved capable of gelating water at concentrations as low as 0.45 mM (=0.03 wt %).

Gelator 12 was dissolved in a small amount of DMSO (100 μL), whereas α-chymotrypsin was dissolved in a buffer solution (Tris-HCl, 0.1 M, pH 7.75, 900 μL). The rapid addition of the aqueous α-chymotrypsin solution to the DMSO solution of 12 resulted in the instantaneous formation of a clear, homogeneous gel that could be used for fluorescence experiments. In order to determine the effect of gelation on the enzymatic cleavage, the water-soluble, non-gelating, model substrate 39 was synthesized with a structure similar to that of gelator 12.

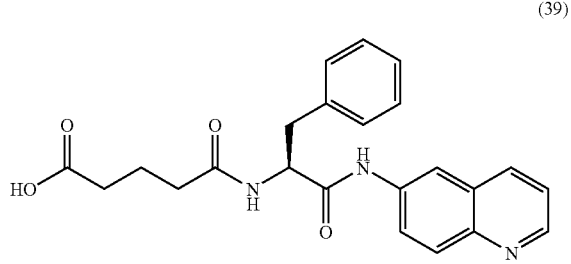

(39)

Figure 2:
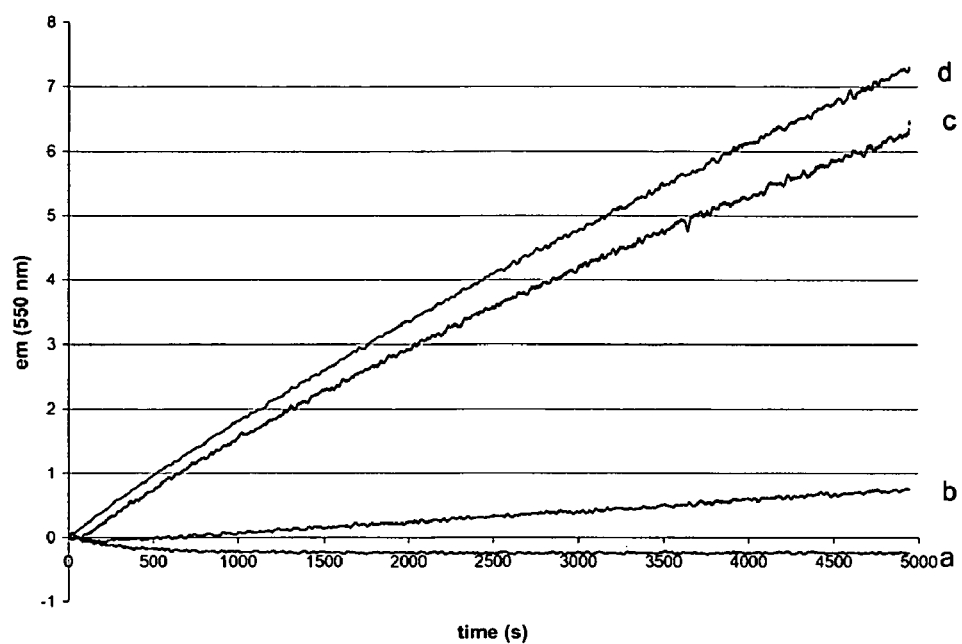
FIG. 2 shows the results of fluorescence experiments carried out wherein the α-chymotrypsin-induced cleavage of compounds was followed through the detection of 6-AQ. This figure shows the formation of 6-AQ over time, as detected by fluorescence at 550 nm ($\lambda_{DK}$=400 nm).

Fluorescence experiments were carried out in which the α-chymotrypsin-induced cleavage of compounds 12 and 39 was followed through the detection of 6-AQ. The results of a set of such measurements are shown in FIG. 2. This figure shows the formation of 6-AQ over time, as detected by fluorescence at 550 nm ($\lambda_{ex}$=400 nm).

Legend to FIG. 2 (from bottom to top): Trace a: gel of gelator 12 (0.5 wt %=7.54 mM); trace b: gel of gelator 12 (0.5 wt %=7.54 mM)+α-chymotrypsin (40 mM); trace c: gel of gelator 12 (0.5 wt %=7.54 mM)+compound 39 (7.54 mM)+α-chymotrypsin (40 μM); trace d: solution of compound 39 (7.54 mM)+α-chymotrypsin (40 mM)

As can be seen, no 6-AQ formation and thus no cleavage is observed for the gelator in the absence of α-chymotrypsin (trace a). Carrying out the same experiment in the presence of α-chymotrypsin (40 mM) resulted in the formation of minor amounts of 6-AQ (trace b) and, therefore, minor cleavage of the gelator. Using a sample containing compound 39 instead of gelator 12, much higher amounts of 6-AQ were detected, proving that the compound was more readily cleaved by α-chymotrypsin (trace c). Finally, carrying out the experiment using a sample containing both the gelator 12 and non-gelator 39 (both in concentrations identical to the ones used for the previous experiments) led to trace d. The amount of 6-AQ detected clearly indicates that the presence of a gel network does not stop α-chymotrypsin from functioning as it does in a non-gelated sample.

Figure 3:
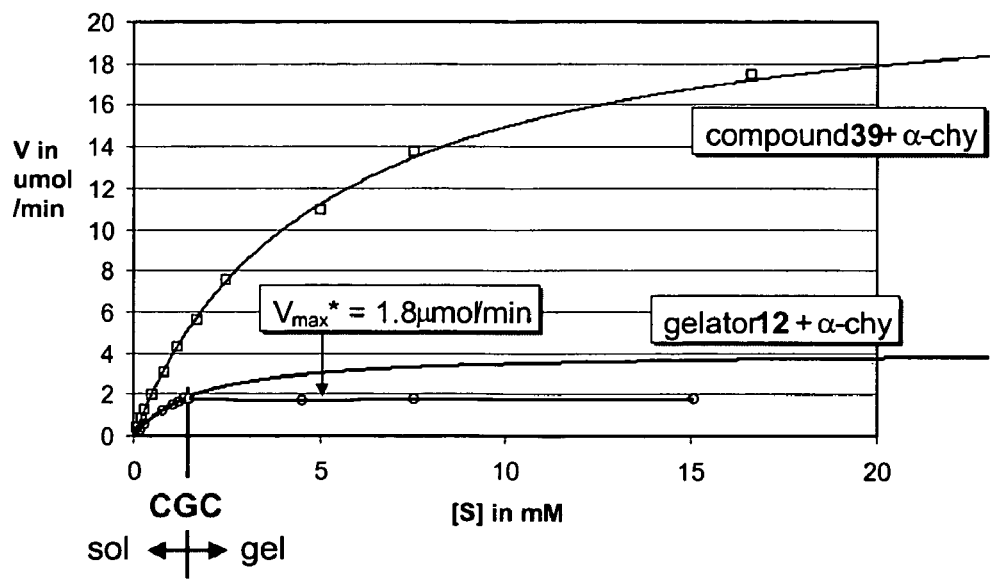
FIG. 3 shows the result of performing cleavage experiments for the compounds at different substrate concentrations and plotting the initial rates as a function of the substrate concentration results in the point plotted.

Performing the cleavage experiments for both 12 and 39 at different substrate concentrations and plotting the initial rates as a function of the substrate concentration (i.e., 12 or 39) results in the points plotted in FIG. 3. This figure shows initial rate as a function of the concentration of substrate (S), with substrates being compound 39 or gelator 12. As can be seen, the values for the initial rates of compound 39 increase as expected when increasing the concentration. The initial rates for gelator 12, however, increase up to a certain point, after which they remain the same, even at much higher concentrations. From the corresponding Lineweaver-Burke and Eadie-Hofstee plots, values for $V_{max}$ and $K_m$ could be obtained for both compounds. For compound 39, the following values were obtained: $V_{max}$=22.3 μmol/min, $K_m$=4.9 mM. For gelator 12, only those points were taken where V still showed an increase with respect to the point before. From these points, the following values were calculated. $V_{max}$=4.1 μmol/min, $K_m$=1.8 mM. Using these values for $V_{max}$ and $K_m$, the theoretical curves could be plotted for both compounds. For compound 39, the experimentally determined points fitted very well on the curve. However, for gelator 12, only part of the points corresponded well to the curve and an experimentally determined $V_{max}$ of 1.8 μmol/min could be determined. Interestingly, the point where the theoretical curve deviated from the experimental curve corresponds to a gelator concentration of 1.5 mM, which again corresponds to the critical gelator concentration (CGC) for 12 in $H_2O$:DMSO=9:1 (i.e., the minimal gelator concentration necessary to give gelation in a solvent or solvent mixture). Below this concentration, a sample of 12 exists as a solution. So, even though the molecules in a gel are in constant equilibrium with those in solution and the overall gelator concentration may increase well above the CGC (thus bringing about gelation), the concentration of gelator in solution can never exceed the CGC. The fact that the initial rate for 12 no longer increases once the substrate (i.e., gelator) concentration exceeds the CGC, proves that only the gelator molecules in solution can be cleaved by the enzyme.

Example IV

Preparation of Gels Containing Particles of a Compound of Interest

IV.1 Inclusion of Pyrene

To a solution containing 4 mg (6.0×10⁻³ mmol) of gelator 12 (CHex(AmPhe-6AQ)(AmEtOEtOH)₂) and 1.22 mg (6.0× 10⁻³ mmol) of pyrene in 100 μL of DMSO, 900 μL of distilled water were quickly added. The addition of water resulted in the immediate and complete gelation of the solution. TEM analysis of the gel shows the presence of gel fibers and pyrene particles, the latter with average size between 37 and 185 nm.

Time-dependent Particle Size Determination

To determine the stability in time of pyrene particles in a gel, samples were prepared as described in the previous paragraph and examined with TEM after 7 days, 18 days, 1 month and 2 months. As reference, samples containing only pyrene in $DMSO/H_2O$ (100 μL/900 μL) were also prepared. Moreover, to determine the effect of the gelator in solution, i.e., not in the gel, samples containing 4 mg (6.0×10⁻³ mmol) of gelator 12 (CHex(AmPhe-6AQ)(AmEtOEtOH)₂), 1.22 mg (6.0×10⁻³ mmol) of pyrene, 100 μL of DMSO and 900 μL of 1N HCl were prepared. The presence of HCl causes the gelator to dissolve and, therefore, the sample does not gelate. All samples were kept at room temperature, in the dark. TEM results are shown in FIGS. 4, 5 and 6.

Figure 4:
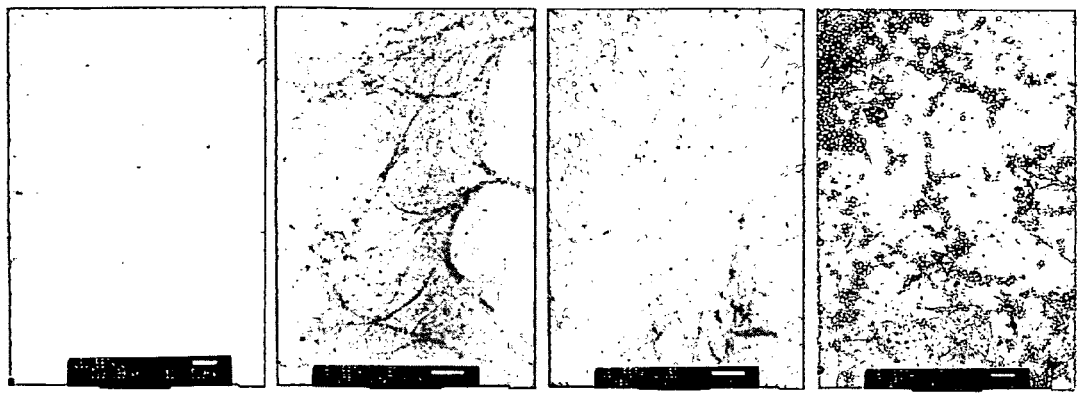
FIG. 4 are TEM images of gels of (Chex(AmPhe-6AQ× AmE(OetOH0$_2$) containing pyrene in a 1:1 molar ratio (6.0× 10$^3$ mmol), in DMSO/H$_2$O (100 µL/900 µL), examined after 7 days, 18 days, 1 month, and 2 months, respectively, from left to right.

FIG. 4: TEM images of gels of 12 (CHex(AmPhe-6AQ)(AmEtOEtOH)₂) containing pyrene in a 1:1 molar ratio (6.0×10⁻³ mmol), in $DMSO/H_2O$ (100 μL/900 μL), examined after 7 days, 18 days, 1 month and 2 months, respectively, from left to right. After seven days, only very few particles, 37-185 nm, are present in the sample; after 18 days, more particles, 30-190 nm, can be observed; after one month, also some crystals, ~150 nm, can be observed; after two months, more crystals with sizes ranging from 80 to 200 nm are present.

Figure 5:
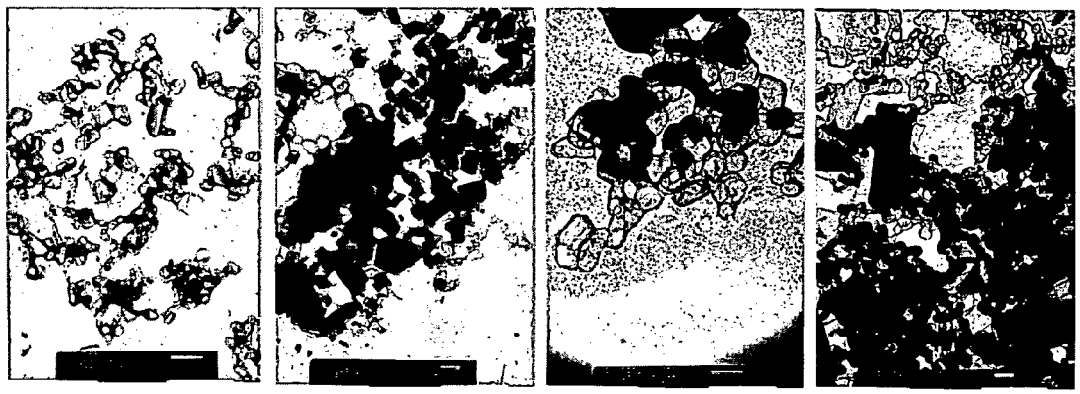
FIG. 5 are TEM images of samples containing (Chex(Am-Phe-6AQ)(AmEtOEtOH)$_2$)and pyrene in a 1:1 molar ratio (6.0×10$^3$ mmol), in DMSO/1N HCl (100 μL/900 μL), examined after 7 days, 18 days, 1 month, and 2 months, respectively, from left to right.
Figure 6:
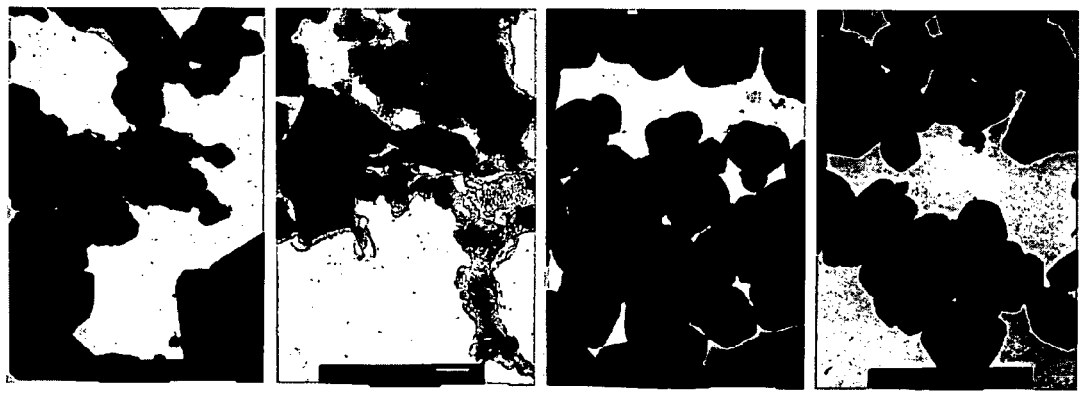
FIG. 6 are TEM images of samples containing pyrene (6.0×10$^{-3}$ mmol), in DMSO/H$_2$O (100 μL/900 μL), examined after 7 days, 18 days, 1 month, and 2 months, respectively, from left to right.
Figure 7:
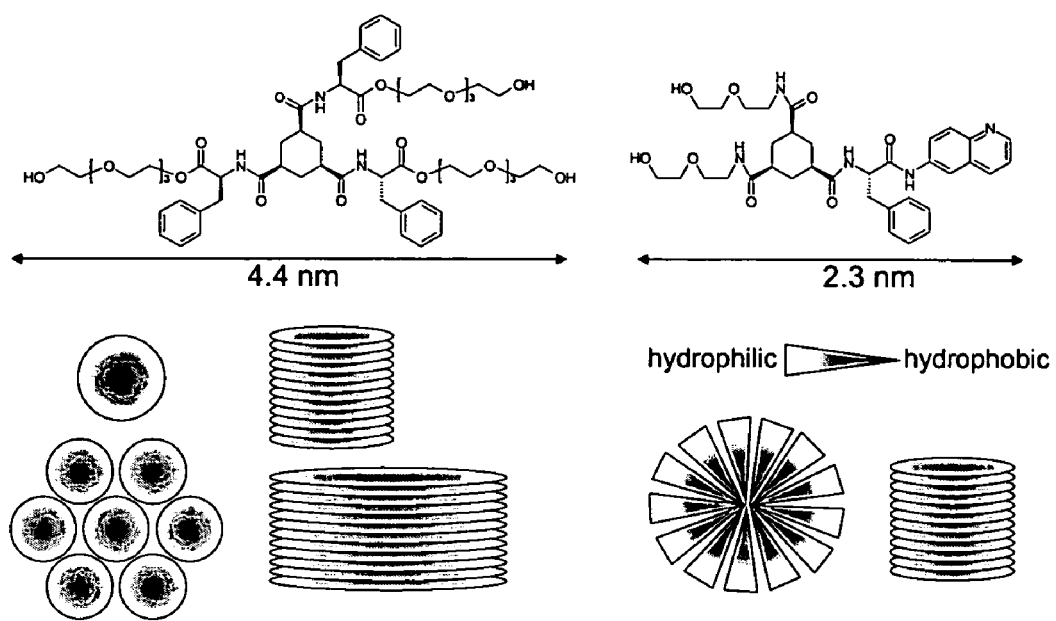
FIG. 7 depicts, right side, a non-symmetrical gelator according to the invention, while the left side depicts a symmetrical gelator.

FIG. 5: TEM images of samples containing 12 (CHex(AmPhe-6AQ)(AmEtOEtOH)₂) and pyrene in a 1:1 molar ratio (6.0×10⁻³ mmol), in DMSO/1N HCl (100 μL/900 μL), examined after 7 days, 18 days, 1 month and 2 months, respectively, from left to right.

After seven days, crystals, 0.2-3 μm, can be observed; after 18 days, more of such crystals can be observed; after 1 month, also larger crystals, 6 μm, can be seen; after 2 months, more of such crystals can be observed.

FIG. 6: TEM images of samples containing pyrene (6.0×10⁻³ mmol), in $DMSO/H_2O$ (100 μL/900 μL), examined after 7 days, 18 days, 1 month and 2 months, respectively, from left to right.

After 7 days, 18 days or 1 month, crystals, 0.4-9 μm, are present; after two months crystals, 2-12 μm, can be observed.

IV.2 Inclusion of Danazol, I

To a solution containing 1.96 mg ($2.9 \times 10^{-3}$ mmol) of gelator 12 (CHex(AmPhe-6AQ)(AmEtOEtOH)$_2$) and 1.0 mg ($2.9 \times 10^{-3}$ mmol) of danazol in 50 μL of DMSO, 950 μL of distilled water were quickly added. The addition of water resulted in the immediate and complete gelation of the solution. TEM analysis of the gel shows the presence of gel fibers and of danazol particles, the latter with average size between 140-700 nm; some rod-shaped danazol particles 0.7 μm wide and 9 μm long were also present. In a reference sample consisting only of danazol in 100 μL of DMSO and 900 μL of distilled water, rod-shaped danazol particles are 0.5-10 μm wide and 15-53 μm long.

IV.3 Inclusion of Danazol, II

When the molar ratio of gelator to danazol in the previous example is increased from 1:1 to 2:1, TEM analysis shows the presence of gel fibers and of danazol particles, the latter with an average size of 28 nm; some particles are 2 μm and very few particles are 10 μm; no rod-shaped danazol particles are present. When the molar ratio is increased again from 2:1 to 5:1, TEM analysis shows the presence of gel fibers and of danazol particles, the latter with an average size of 14 nm, some particles are 400 nm, and no rod-shaped particles are present.

Freeze Drying of a Gel Containing Danazol

Freeze-drying of a gel containing gelator 12 (CHex(AmPhe-6AQ)(AmEtOEtOH)$_2$) and danazol in a 5:1 molar ratio, in DMSO/water (50 μL/950 μL) yields a dry powder of gelator and danazol. TEM analysis of this powder shows similar features to the corresponding gel sample (previous example): gel fibers and danazol particles, the latter with an average size of 14 to 70 nm, no rod-shaped particles were present.

What is claimed is:

1. A method of thickening a fluid, comprising:
incorporating into said fluid a trisubstituted cyclic compound, of which the ring is substituted by one or two X—Am—Y$_n$ groups and wherein the remaining one or two substituents are —X-Z groups, wherein the substituted ring is a 1,3,5-substituted cyclohexane, the compound being non-symmetrical in that at least one of said —X-Z groups is free of an Am moiety, wherein
each of X is independently chosen from the moieties —N(H)—, —C(O)—, —O(CO)—, —OC(S)—, —C(S)—, —NHC(S)—, and —NH—C(O)—;
each of Am is independently a moiety based on an amino acid or on an amino acid derivative, or on a number of amino acids or derivatives thereof;
each of Y is independently chosen from the group of —OR, —N(OH)R, —NR$_2$, —C(O)R, —C(O)—NR$_2$, —C(O)—OR, —C(S)R, —C(S)—NR$_2$, —C(S)—OR, and R, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms;
each Z is independently selected from the group consisting of —OH, —COOH, —C(O)NHR, —NHC(O)R and —NHR, wherein each R is independently chosen, and defined as above; and
n=1 or 2
as a gelator or thickener.

2. A non-symmetrical, trisubstituted cyclic thickener or gelator, of which a ring thereof is substituted by one or two X—Am—Y$_n$ groups and wherein remaining one or two substituents are —X-Z groups, wherein the substituted ring is a 1,3,5-substituted cyclohexane the compound being non-symmetrical in that at least one of said —X-Z groups is free of an Am moiety, wherein
each of X is independently chosen from the moieties —N(H)—, —C(O)—, —O(CO)—, —OC(S)—, —C(S)—, —NHC(S)—, and —NH—C(O)—;
each of Am is independently a moiety based on an amino acid or on an amino acid derivative, or on a number of amino acids or derivatives thereof;
each of Y is independently chosen from the group of —OR, —N(OH)R, —NR$_2$, —C(O)R, —C(O)—NR$_2$, —C(O)—OR, —C(S)R, —C(S)—NR$_2$, —C(S)—OR, and R, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms;
each Z is independently selected from the group consisting of —OH, —COOH, —C(O)NHR, —NHC(O)R and —NHR, wherein each R is independently chosen, and defined as above; and
n=1 or 2,
with the proviso that the thickener of gelator is not

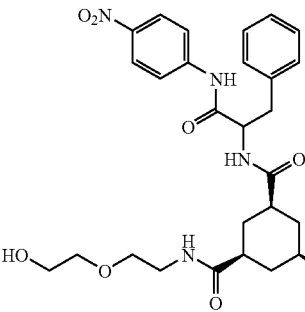

3. The trisubstituted thickener or gelator of claim 2, being free of a zwitter-ionic couple formed by a carboxylic acid group and an amine group.

4. The trisubstituted thickener or gelator of claim 2, wherein each of Am comprises 1 to 5 amino acid residues.

5. The trisubstituted thickener or gelator of claim 2, wherein the substituted ring is a trisubstituted cyclohexane.

6. The trisubstituted thickener or gelator of claim 2, wherein each Y is independently chosen from the group of —OH, —OCH$_3$, —OCH$_2$CH$_3$, —NHCH$_3$, branched and linear —NH(CH$_2$)$_{x+1}$, wherein x is an integer from 1-9, branched and linear NHC(CH$_3$)(CH$_2$)$_{y+1}$CH$_3$, wherein y is an integer from 0-7, —NH(CH$_2$)$_9$CH$_3$, —NH(CH$_2$)$_{10}$CH$_3$, —NHC(CH$_3$)(CH$_2$)$_5$(CH$_3$), —NH-Naphthyl, —NHCH$_2$Ph, —NH(CH$_2$)$_2$Ph, —NHPhOMe, —NH-Quinoline and NHPhNO$_2$.

7. The trisubstituted thickener or gelator of claim 2, wherein the X in the X-Z group or groups and the X in the —X—Am—(Y)$_n$ group or groups is —C(O)—.

8. The trisubstituted thickener or gelator of claim 2, wherein each Z is independently selected from the group consisting of OH, COOH, C(O)NHR, NHC(O)R and NHR, wherein each R is independently chosen, and wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms.

9. The trisubstituted thickener or gelator of claim 8, wherein —X-Z is chosen from the groups of —COOH, —C(O)—NH$_2$, —C(O)—NHCH$_3$, —C(O)—NH—(CH$_2$)$_2$—OH, —C(O)—NH—(CH$_2$)$_2$—O—(CH$_2$)$_2$—OH, C(O)OCH$_2$Ph and —C(O)NHCH$_2$-pyr.

10. The trisubstituted thickener or gelator of claim 2, wherein the amino acids are chosen from the group of α-amino acids, preferably from the group consisting of leucine, isoleucine, norleucine, lysine, valine, proline, methionine, glycine, histidine, alanine, phenylalanine, tryptophan, serine, threonine, cysteine, tyrosine, asparagine, glutamine, aspartic acid, glutamic acid, arginine, and derivatives thereof.

11. The trisubstituted thickener or gelator of claim 2, wherein at least one of the substituents comprises a cleavable moiety, which, upon cleavage, results in the release of a substance of interest.

12. The trisubstituted thickener or gelator of claim 11, wherein the substance of interest is linked via a linker comprising an amino acid moiety that is enzymatically cleavable at its C=O terminus.

13. A method of gelating or thickening a solvent, said method comprising:
mixing the trisubstituted thickener or gelator of claim 2 with the solvent and triggering the mixture to obtain the thickened or gelated solvent.

14. A method of gelating or thickening a solvent, said method comprising:
spraying the trisubstituted thickener or gelator of claim 2 into the solvent in the form of a solution, or
spraying the solvent into a solution of the trisubstituted thickener or gelator or complex.

15. The method according to claim 14, wherein the solvent is selected from the group consisting of aromatic hydrocarbons, non-aromatic hydrocarbons, alcohols, ethers, esters, aldehydes, ketones, alkanoic acids, epoxides, amines, halogenated hydrocarbons, silicon oils, vegetable oils, phosphoric acids, sulfoxides, amides, nitrites, water and mixtures thereof, preferably from the group consisting of aromatic hydrocarbons, aliphatic hydrocarbons, alcohols, esters, halogenated hydrocarbons, ethers, vegetable oils, water, ketones, amides, nitrites, and mixtures of any thereof.

16. The method according to claim 13, wherein the gelling agent or thickener is mixed with, or sprayed into the solvent in an amount between 0.01 and 50 wt. %, based on the weight of the resultant mixture.

17. The method according to claim 13, wherein the formation of a gel is triggered by heating the mixture followed by:
cooling,
changing the pH,
sonication,
use of light and/or
adding a chemical inducer.

18. The method according to claim 17, wherein the mixture is heated to a temperature of 20-200° C.

19. The method according to claim 17, wherein the mixture is cooled to a temperature in the range of from −20 to 100° C.

20. A gel or thickened fluid, comprising one or more trisubstituted thickener or gelators of claim 2.

21. A gel or thickened fluid comprising
(i) one or more of the trisubstituted thickeners or gelators of claim 2, and
(ii) one or more solvents.

22. A chromatographic support comprising:
the gel or thickened fluid of claim 20,
wherein the chromatographic support is used in a process for chiral recognition, for covalent binding of a catalyst, or as drug delivery vehicle.

23. A composition for use as a pharmaceutical, said composition comprising:
a gel or thickened fluid, wherein said gel or thickened fluid comprises:
the thickener or gelator of claim 2, and
a pharmaceutically active agent.

24. A composition for use as a cosmetic, said composition comprising a gel or thickened fluid, wherein said gel or thickened fluid comprises the thickener or gelator of claim 2.

25. The composition of claim 23 wherein the composition is selected from the group consisting of deodorants, compositions for topical application and compositions for application to the eye.

26. The trisubstituted thickener or gelator of claim 12 wherein said amino acid moiety is based on phenylalanine and said substance of interest is a biologically active agent.

* * * * *